US 6,743,939 B2

(12) United States Patent
Birkinshaw et al.

(10) Patent No.: US 6,743,939 B2
(45) Date of Patent: Jun. 1, 2004

(54) PHENYLHETEROALKYLAMINE DERIVATIVES

(75) Inventors: Tim Birkinshaw, Loughborough (GB); David Cheshire, Loughborough (GB); Antonio Mete, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/204,815

(22) PCT Filed: Feb. 20, 2001

(86) PCT No.: PCT/SE01/00370

§ 371 (c)(1),
(2), (4) Date: Aug. 22, 2002

(87) PCT Pub. No.: WO01/62713

PCT Pub. Date: Aug. 30, 2001

(65) Prior Publication Data

US 2003/0105161 A1 Jun. 5, 2003

(30) Foreign Application Priority Data

Feb. 23, 2000 (GB) ................................ 0004149

(51) Int. Cl.[7] ...................... A61K 31/277; C07C 255/50
(52) U.S. Cl. ........................................ 558/422; 514/524
(58) Field of Search ........................... 514/524; 558/422

(56) References Cited

U.S. PATENT DOCUMENTS 4,296,126 A   10/1981   Nedelec et al.
4,314,081 A   2/1982    Molloy et al.
4,902,710 A   2/1990    Foster et al.

FOREIGN PATENT DOCUMENTS

| DE | 29 07 217 A1  | 8/1979  |
| EP | 0 273 658 B1  | 7/1988  |
| EP | 0 576 766 A1  | 1/1994  |
| JP | 51044934 B4   | 12/1976 |
| JP | 52000941 B4   | 1/1977  |
| WO | WO 92/19210   | 11/1992 |
| WO | WO 99/10339   | 3/1999  |
| WO | WO 99/11620   | 3/1999  |
| WO | WO 99/62883   | 12/1999 |

OTHER PUBLICATIONS

S.J. Yan, et al. "Potential causal prophylactic antimalarial agents. Synthesis of quinoxaline, benzimidazole, and alkoxybenzene derivatives containing a novoldiamine moiety." J. Heterocycl. Chem. 297–300, (1978).

Primary Examiner—Taofiq Solola
(74) Attorney, Agent, or Firm—Fish & Richardson P.C.

(57) ABSTRACT

There are provided novel compounds of formula (I), wherein $R^1$, $R^2$, X, Y, V, W and Z are as defined in the specification, and pharmaceutically acceptable salts thereof, and enantiomers and racemates thereof; together with processes for their preparation, compositions containing them and their use in therapy. The compounds are inhibitors of nitric oxide synthase and are thereby particularly useful in the treatment or prophylaxis of inflammatory disease and pain.

29 Claims, No Drawings

PHENYLHETEROALKYLAMINE DERIVATIVES

CROSS REFERENCE TO RELATED APPLICATIONS

The present application is a national phase application under 35 U.S.C. Section 371 filed from International Patent Application PCT/SE01/00370, filed Feb. 20, 2001. The contents of the applications are incorporated herein by reference in their entirety.

FIELD OF THE INVENTION

The present invention relates to novel phenylheteroalkylamine derivatives, processes for their preparation, compositions containing them and their use in therapy.

BACKGROUND OF THE INVENTION

Nitric oxide is produced in mammalian cells from L-arginine by the action of specific nitric oxide synthases (NOSs). These enzymes fall into two distinct classes—constitutive NOS (cNOS) and inducible NOS (iNOS). At the present time, two constitutive NOSs and one inducible NOS have been identified. Of the constitutive NOSs, an endothelial enzyme (ecNOS) is involved with smooth muscle relaxation and the regulation of blood pressure and blood flow, whereas the neuronal enzyme (ncNOS) serves as a neurotransmitter and appears to be involved in the regulation of various biological functions such as cerebral ischaemia. Inducible NOS has been particularly implicated in the pathogenesis of inflammatory diseases. Regulation of these enzymes should therefore offer considerable potential in the treatment of a wide variety of disease states (J. E. Macdonald, *Ann. Rep. Med. Chem.*, 1996, 31, 221–230).

Considerable effort has been expended in efforts to identify compounds that act as specific inhibitors of one or more isoforms of the enzyme nitric oxide synthase. The use of such compounds in therapy has also been widely claimed.

DISCLOSURE OF THE INVENTION

According to the present invention, there is provided a compound of formula (I)

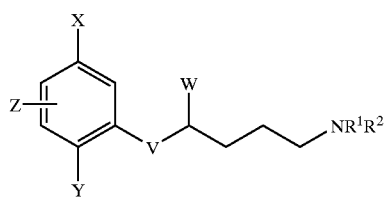
(I)

wherein:
- X and Y independently represent C1 to 4 alkyl, C1 to 4 alkoxy, halogen, $CF_3$, $OCF_3$, CN, C≡CH, $S(O)_mCH_3$, $S(O)_pCF_3$, $NO_2$ or NHCHO;
- m and p independently represent an integer 0, 1 or 2;
- Z represents H or fluoro;
- V represents O, $S(O)_n$ or $NR^3$;
- W represents C1 to 4 alkyl, C2 to 4 alkenyl, C2 to 4 alkynyl, C3 to 6 cycloalkyl or a 4 to 8 membered saturated heterocyclic ring incorporating one heteroatom selected from O, S and N; any of said groups being optionally further substituted by C1 to 4 alkyl, C1 to 4 alkoxy, C1 to 4 alkylthio, C3 to 6 cycloalkyl; halogen or phenyl; said phenyl group being optionally further substituted by one or more substituents selected independently from halogen, C1 to 4 alkyl, C1 to 4 alkoxy, $CF_3$, $OCF_3$, CN or $NO_2$;
- or W represents phenyl or a five or six membered aromatic heterocyclic ring containing 1 to 3 heteroatoms independently selected from O, S and N; said phenyl or aromatic heterocyclic ring being optionally substituted by one or more substituents selected independently from halogen, C1 to 4 alkyl, C1 to 4 alkoxy, OH, CN, $NO_2$ or $NR^4R^5$; said alkyl or alkoxy group being optionally further substituted by one or more fluorine atoms;
- $R^1$ and $R^2$ independently represent H, C1 to 4 alkyl or C3 to 6 cycloalkyl; said alkyl group being optionally substituted by C1 to 4 alkoxy, halogen, hydroxy, $NR^6R^7$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, $CF_3$, $OCF_3$, CN or $NO_2$;
- or the group $NR^1R^2$ together represents a 4 to 8 membered saturated azacyclic ring optionally incorporating one further heteroatom selected from O, S or $NR^8$; said ring being optionally substituted by C1 to 4 alkyl, C1 to 4 alkoxy or OH; said alkyl group being optionally substituted by C1 to 4 alkoxy, OH or $NR^9R^{10}$;
- or the group $NR^1 R^2$ together represents part of a five membered aromatic azacyclic ring optionally incorporating one further N atom;
- $R^3$ represents H or C1 to 4 alkyl;
- $R^4$, $R^5$, $R^6$, $R^7$, $R^9$ and $R^{10}$ independently represent H or C1 to 4 alkyl;
- $R^8$ represents H or C1 to 6 alkyl; said alkyl group being optionally substituted by C1 to 4 alkoxy, OH, $NR^{11}R^{12}$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, $CF_3$, $OCF_3$, CN or $NO_2$;
- $R^{11}$ and $R^{12}$ independently represent H or C1 to 4 alkyl;
- n represents an integer 0, 1 or 2;
- or a pharmaceutically acceptable salt, enantiomer or racemate thereof.

The compounds of formula (I) and their pharmaceutically acceptable salts, enantiomers and racemates have the advantage that they are inhibitors of the enzyme nitric oxide synthase (NOS). In particular, the compounds of formula (I) and their pharmaceutically acceptable salts, enantiomers and racemates have the advantage that they are inhibitors of the inducible isoform of the enzyme nitric oxide synthase (iNOS).

The invention further provides a process for the preparation of compounds of formula (I) or a pharmaceutically acceptable salt, enantiomer or racemate thereof.

According to the invention there is also provided a compound of formula (I), or a pharmaceutically acceptable salt, enantiomer or racemate thereof, for use as a medicament.

Another aspect of the invention provides the use of a compound of formula (I) or a pharmaceutically acceptable salt, enantiomer or racemate thereof, in the manufacture of a medicament, for the treatment or prophylaxis of diseases or conditions in which inhibition of nitric oxide synthase activity is beneficial.

A more particular aspect of the invention provides the use of a compound of formula (I) or a pharmaceutically acceptable salt, enantiomer or racemate thereof, in the manufacture of a medicament, for the treatment or prophylaxis of inflammatory disease.

According to the invention, there is also provided a method of treating, or reducing the risk of, diseases or conditions in which inhibition of nitric oxide synthase activity is beneficial which comprises administering to a person suffering from or at risk of, said disease or condition, a therapeutically effective amount of a compound of formula (I) or a pharmaceutically acceptable salt, enantiomer or racemate thereof.

More particularly, there is also provided a method of treating, or reducing the risk of, inflammatory disease in a person suffering from or at risk of, said disease, wherein the method comprises administering to the person a therapeutically effective amount of a compound of formula (I) or a pharmaceutically acceptable salt, enantiomer or racemate thereof.

The compounds of the present invention may also be used advantageously in combination with a second pharmaceutically active substance, particularly in combination with a selective inhibitor of the inducible isoform of cyclooxygenase (COX-2). Thus, in a further aspect of the invention there is provided the use of a compound of formula (I) or a pharmaceutically acceptable salt, enantiomer or racemate thereof, in combination with a COX-2 inhibitor for the treatment of inflammation, inflammatory disease and inflammatory related disorders. And there is also provided a method of treating, or reducing the risk of, inflammation, inflammatory disease and inflammatory related disorders in a person suffering from or at risk of, said disease or condition, wherein the method comprises administering to the person a therapeutically effective amount of a compound of formula (I) or a pharmaceutically acceptable salt, enantiomer or racemate thereof in combination with a COX-2 inhibitor.

In one preferred embodiment, V represents O. In another preferred embodiment, V represents S.

In another preferred embodiment, X and Y independently represent Br, Cl, $CH_3$, $CF_3$ or CN. It is particularly preferred that X represents Cl or $CF_3$. It is also particularly preferred that Y represents Cl, CN or $CF_3$.

Preferably, W represents an optionally substituted five or six membered aromatic heterocyclic ring containing 1 to 3 heteroatoms independently selected from O, S and N. Particular examples are those wherein W represents thienyl, furyl, imidazolyl, pyridyl, thiazolyl or triazolyl.

Preferably, $R^1$ and $R^2$ independently represent H or Cl to 4 alkyl optionally substituted by Cl to 4 alkoxy or hydroxy. More preferably, $R^1$ and $R^2$ independently represent H or methyl.

Particular compounds of the invention include:
4-chloro-2-[[(1R)-4-(methylamino)-1-phenylbutyl]oxy] benzonitrile;
R-γ-(2,5-dichlorophenoxy)-N-methyl-benzenebutanamine;
4-chloro-2-[[(1R)-1-phenyl-4-(1-pyrrolidinyl)butyl]oxy]-benzonitrile;
4-chloro-2-[[(1R)-4-(4-morpholinyl)-1-phenylbutyl] oxy]-benzonitrile;
4-chloro-2-[[(1R)-4-[ethyl(2-hydroxyethyl)amino]-1-phenylbutyl]oxy]-benzonitrile;
4-chloro-2-[[(1R)-1-phenyl-4-[(3-pyridinylmethyl) amino]butyl]oxy]-benzonitrile;
4-chloro-2-[[(1R)-4-[[2-(1H-imidazol-5-yl)ethyl]amino]-1-phenylbutyl]oxy]-benzonitrile;
4-chloro-2-[[(1R)-4-(1H-imidazol-1-yl)-1-phenylbutyl] oxy]-benzonitrile;
4-chloro-2-[[(1R)-4-[(2-hydroxyethyl)amino]-1-phenylbutyl]oxy]-benzonitrile;
4-chloro-2-[[(1R)-4-(cyclopropylamino)-1-phenylbutyl] oxy]-benzonitrile;
4-chloro-2-[[(1R)-4-[(3-hydroxypropyl)amino]-1-phenylbutyl]oxy]-benzonitrile;
4-chloro-2-[[(1R)-4-[[(1R)-2-hydroxy-1-methylethyl] amino]-1-phenylbutyl]oxy]-benzonitrile;
4-chloro-2-[[(1R)-4-[[(1S)-2-hydroxy-1-methylethyl] amino]-1-phenylbutyl]oxo]-benzonitrile;
4-chloro-2-[4-[[(2-fluoroethyl)amino]-1-phenylbutyl] oxy]-benzonitrile;
R-δ-(2,5-dichlorophenoxy)-4-fluoro-N-methyl-benzenebutanamine;
S-δ-(2,5-dichlorophenoxy)-4-fluoro-N-methyl-benzenebutanamine;
R-γ-(2,5-dichlorophenoxy)-N,4-dimethyl-benzenebutanamine;
S-γ-(2,5-dichlorophenoxy)-N,4-dimethyl-benzenebutanamine;
δ-(2,5-dichlorophenoxy)-N-methyl-2-thiophenebutanamine;
2-[(4-amino-1-phenylbutyl)amino]-4-chloro-benzonitrile;
2-[[1-(3-aminopropyl)-3-methylbutyl]amino]-4-(trifluoromethyl) benzonitrile;
2-[[4-(2,5-dichlorophenoxy)-4-phenylbutyl] methylamino]ethanol;
1-[4-(2,5-dichlorophenoxy)-4-phenylbutyl]-4-piperidinol;
1-[4-(2,5-dichlorophenoxy)-4-phenylbutyl]piperazine;
1-[4-(2,5-dichlorophenoxy)-4-(2-thienyl)butyl]4-methyl-piperazine;
4-chloro-2-[4-(methylamino)-1-(3-thienyl)butoxy]-benzonitrile;
4-chloro-2-[1-(3-furanyl)-4-(methylamino)butoxy] benzonitrile;
2-[4-amino-1-(3-furanyl)butoxy]-4-chlorobenzonitrile;
4-chloro-2-[1-(2-furanyl)-4-(methylamino)butoxy] benzonitrile;
2-[[(1R)-4-amino-1-(1-methyl-1H-imidazol-2-yl)butyl] oxy]-4-chloro-5-fluorobenzonitrile;
4-chloro-2-[4-(methylamino)-1-(2-pyridinyl)butoxy] benzonitrile;
4-chloro-5-fluoro-2-[4-(methylamino)-1-(2-pyridinyl) butoxy]benzonitrile;
4-chloro-2-[4-(ethylamino)-1-(2-pyridinyl)butoxy] benzonitrile;
2-[4-amino-1-(3-pyridinyl)butoxy]-4-chloro-benzonitrile;
4-chloro-2-[4-(methylamino)-1-(3-pyridinyl)butoxy]-benzonitrile;
4-chloro-2-[4-(ethylamino)-1-(4-pyridinyl)butoxy]-benzonitrile;
4-chloro-2-[4-(methylamino)-1-(4-pyridinyl)butoxy] benzonitrile;
4-chloro-2-[4-[(2-hydroxyethyl)amino]-1-(4-pyridinyl) butoxy]benzonitrile;

2-[4-amino-1-(2-methoxy-3-pyridinyl)butoxy]-4-chloro-benzonitrile;
2-[4-amino-1-(1,2-dihydro-2-oxo-3-pyridinyl)butoxy]-4-chlorobenzonitrile;
2-[[(1R)-4-amino-1-(3-furanyl)butyl]oxy]-4-chloro-5-fluoro-benzonitrile;
4-chloro-5-fluoro-2-[[(1R)-1-(3-furanyl)-4-(methylamino)butyl]oxy]benzonitrile;
2-[4-amino-1-(2-thiazolyl)butoxy]-4-chlorobenzonitrile;
δ-[2-chloro-5-(trifluoromethyl)phenoxy]-2-thiazolebutanamine;
2-[4-amino-1-(1-methyl-1H-1,2,4-triazole-5-yl)butoxy-4-chlorobenzonitrile;
δ-[2-chloro-5-(trifluoromethyl)phenoxy]-1-methyl-1H-1,2,4-triazole-5-butanamine;
and pharmaceutically acceptable salts, enantiomers or racemates thereof.

Unless otherwise indicated, the term "C1 to 4 alkyl" referred to herein denotes a straight or branched chain alkyl group having from 1 to 4 carbon atoms. Examples of such groups include methyl, ethyl, n-propyl, i-propyl, n-butyl, i-butyl and t-butyl.

The term "C1 to 6 alkyl" is to be interpreted analogously.

Unless otherwise indicated, the term "C3 to 6 cycloalkyl" referred to herein denotes a cycloalkyl group having from 3 to 6 carbon atoms. Examples of such groups include cyclopropyl, cyclopentyl and cyclohexyl.

Unless otherwise indicated, the term "C2 to 4 alkenyl" referred to herein denotes a straight or branched chain alkyl group having from 2 to 4 carbon atoms incorporating at least one carbon-carbon double bond. Examples of such groups include ethenyl, propenyl and butenyl.

Unless otherwise indicated, the term "C2 to 4 alkynyl" referred to herein denotes a straight or branched chain alkyl group having from 2 to 4 carbon atoms incorporating at least one carbon-carbon triple bond. Examples of such groups include ethynyl, propynyl, and butynyl.

Unless otherwise indicated, the term "C1 to 4 alkoxy" referred to herein denotes a straight or branched chain alkoxy group having from 1 to 4 carbon atoms. Examples of such groups include methoxy, ethoxy, n-propoxy, i-propoxy and t-butoxy.

The term "C1 to 4 alkylthio" is to be interpreted analogously.

Unless otherwise indicated, the term "halogen" referred to herein denotes fluoro, chloro, bromo and iodo.

Examples of a 4 to 8 membered saturated azacyclic ring optionally incorporating one further heteroatom selected from O, S or N include pyrrolidine, piperidine, piperazine, morpholine and perhydroazepine.

Examples of a 4 to 8 membered saturated heterocyclic ring incorporating one heteroatom selected from O, S or N include pyrrolidine, piperidine, tetrahydrofuran and perhydroazepine.

Examples of a five or six membered aromatic heterocyclic ring containing 1 to 3 heteroatoms independently selected from O, S and N include furan, thiophene, pyridine, thiazole, imidazole, oxazole, triazole, oxadiazole, thiadiazole and pyrimidine.

Examples of a five or six membered saturated heterocyclic ring containing 1 to 3 heteroatoms independently selected from O, S and N include pyrrolidine, tetrahydrofuran, piperidine and piperazine.

Examples of a "C1 to 4 alkyl or C1 to 4 alkoxy optionally further substituted by one or more fluorine atoms" include $CF_3$, $CF_3CF_2$, $CF_3CH_2$, $CH_2FCH_2$, $CH_3CF_2$, $CF_3CH_2CH_2$, $OCF_3$ and $OCH_2CF_3$.

Examples of a five membered aromatic azacyclic ring optionally incorporating one further N atom include pyrrole and imidazole.

According to the invention, we further provide a process for the preparation of compounds of formula (I), or a pharmaceutically acceptable salt, enantiomer or racemate thereof which comprises:

(a) reaction of a compound of formula (II)

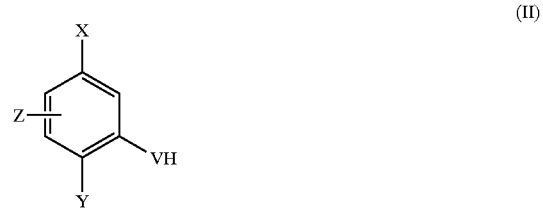

(II)

wherein X, Y, V and Z are as defined in formula (I), with a compound of formula (III)

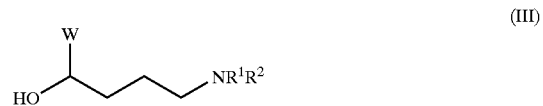

(III)

wherein W, $R^1$ and $R^2$ are as defined in formula (I); or (b) reaction of a compound of formula (IV)

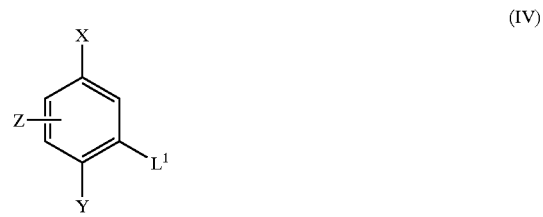

(IV)

wherein X, Y and Z are as defined in formula (I) and $L^1$ represents a leaving group, with a compound of formula (V)

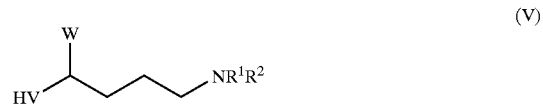

(V)

wherein $R^1$, $R^2$, V and W are as defined in formula (I); or (c) reaction of a compound of formula (VI)

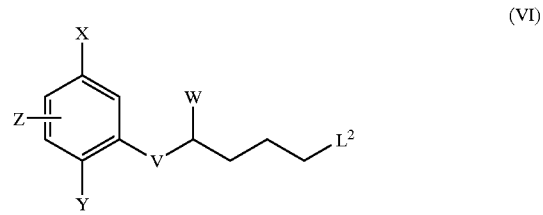

(VI)

wherein X, Y, V, W and Z are as defined in formula (I) and $L^2$ is a leaving group, with a compound of formula (VII)

$HNR^1R^2$ (VII)

wherein $R^1$ and $R^2$ are as defined in formula (I); or (d) reaction of a compound of formula (II)

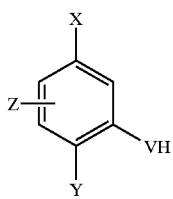

wherein X, Y, V and Z are as defined in formula (I), with a compound of formula (VIII)

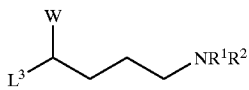

wherein $R^1$, $R^2$ and W are as defined in formula (I) and $L^3$ is a leaving group; or (e) reduction of a compound of formula (IX)

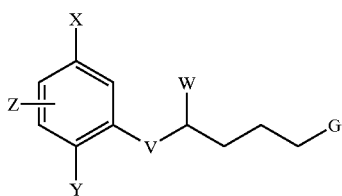

wherein X, Y, V, W and Z are as defined in formula (I) and G represents a group that upon reduction is converted into a group $NR^1R^2$; and where necessary converting the resultant compound of formula (I), or another salt thereof, into a pharmaceutically acceptable salt thereof; or converting the resultant compound of formula (I) into a further compound of formula (I); and where desired converting the is resultant compound of formula (I) into an optical isomer thereof.

In process (a), the reactants (II) and (III) are coupled together in a suitable inert solvent such as tetrahydrofuran using, for example, Mitsunobu conditions. Thus, for example, the reactants are treated with a phosphine derivative and an azo derivative at a suitable temperature, generally between 0° C. and the boiling point of the solvent. Suitable phosphine derivatives include triphenylphosphine and tributylphosphine. Suitable azo derivatives include diethyl azodicarboxylate, diisopropyl azodicarboxylate and 1,1'-(azodicarbonyl)dipiperidine.

In process (b), the reaction is performed by treating a nucleophile of formula (V) with an electrophile of formula (IV) in an inert solvent. Suitable leaving groups $L^1$ include halides, particularly fluoride. The reaction is generally performed in the presence of a non-nucleophilic base such as sodium hydride. Suitable organic solvents are those such as N-methyl-2-pyrrolidinone, tetrahydrofuran and dimethylsulfoxide. The reaction is generally conducted at a temperature between 0° C. and the boiling point of the solvent.

Alternatively, in process (b), the reaction will take place using an appropriate palladium source such as palladium (II) acetate in the presence of a suitable phosphine ligand such as BINAP.

In process (c), the amination reaction is performed by reacting a compound of formula (VI) with an amine (VII) in an inert solvent. Suitable leaving groups $L^2$ include sulfonate, trifluorosulfonate, tosylate and halides selected from the group chloride, bromide or iodide. The nucleophile can be a primary or secondary amine in the presence of a base. This base can be either an excess of the amine nucleophile or can be an additive to the reaction mixture. Potential basic additives are metal carbonate, especially alkali metal carbonates, metal oxides and hydroxides, and tertiary amine bases. Suitable organic solvents are those such as acetonitrile, dioxane, N,N-dimethylformamide, N-methyl-2-pyrrolidinone, tetrahydrofuran, dimethylsulfoxide, sulfolane and C1 to 4 alcohols.

In process (d), the reaction is performed by treating a nucleophile of formula (II) with an. electrophile of formula (VIII) in an inert solvent. Suitable leaving groups $L^3$ include halides, particularly chloride or bromide. The reaction is generally performed in the presence of a non-nucleophilic base such as sodium hydride. Suitable organic solvents are those such as N-methyl-2-pyrrolidinone, tetrahydrofuran and dimethylsulfoxide. The reaction is generally conducted at a temperature between 0° C. and the boiling point of the solvent.

In process (e), G preferably represents an azido ($N_3$) group. The required reduction may then be achieved by treating a compound of formula (IX) with a suitable reducing agent such as Sn(II) or triphenylphosphine. Preferably the reducing agent is triphenylphosphine and the reduction is carried out in a suitable inert solvent such as tetrahydrofuran.

It will be apparent to a person skilled in the art that in the above processes it may be desirable or necessary to protect an amine, hydroxyl or other potentially reactive group. Suitable protecting groups and details of processes for adding and removing such groups may be found by reference to the standard text "Protecting Groups in Organic Synthesis", 2nd Edition (1991) by Greene and Wuts. In one preferred embodiment, amine groups are protected as carbamate derivatives, for example, as t-butyloxycarbamates. Thus, compounds of formula (I) in which $R^1$ is H are conveniently prepared by removal of a carbamate protecting group from a corresponding compound of formula (I) wherein $R^1$ is a carbamate group, especially a t-butyloxycarbamate group. Removal of the carbamate group is conveniently effected using hydrogen chloride in dioxan.

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable acids may be of utility in the preparation and purification of the compound in question. Thus, preferred salts include those formed from hydrochloric, hydrobromic, sulphuric, phosphoric, citric, tartaric, lactic, pyruvic, acetic, succinic, fumaric, maleic, methanesulphonic and benzenesulphonic acids.

Salts of compounds of formula (I) may be formed by reacting the free base, or a salt, enantiomer or racemate thereof, with one or more equivalents of the appropriate acid. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed in vacuo or by freeze drying. The reaction may also be a metathetical process or it may be carried out on an ion exchange resin.

Certain novel intermediates of formulae (III), (V), (VI), (VIII) and (IX) form another aspect of the invention.

Compounds of formula (III) may be prepared by reaction of a compound of formula (X)

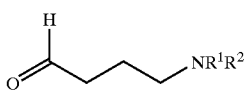
(X)

wherein $R^1$ and $R^2$ are as defined in formula (I), with an organometallic derivative, W—M, wherein W is as defined in formula (I) and M represents a metallic residue such as lithium or magnesium-halide, or M represents a silyl residue such as $SiMe_3$.

Compounds of formula (IX) may be prepared by:
(a) reacting a compound of formula (II), as defined above, with a compound of formula (XI)

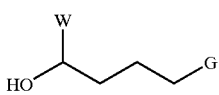
(XI)

wherein W and G are as defined above; or
(b) reacting a compound of formula (IV), as defined above, with a compound of formula (XII)

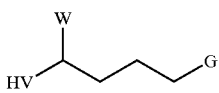
(XII)

wherein V, W and G are as defined above.

Compounds of formulae (II), (IV), (VII), (X), (XI) and (XII) are either known or may be prepared using known methods. Some such methods are illustrated within the Examples that are included herein. Other suitable methods will be readily apparent to the man skilled in the art.

Intermediate compounds may be used as such or in protected form. Protecting groups and details of processes for their removal may be found by reference to the standard text "Protecting Groups in Organic Synthesis", 2nd Edition (1991) by Greene and Wuts.

The compounds of the invention and intermediates thereto may be isolated from their reaction mixtures and, if necessary further purified, by using standard techniques.

The compounds of formula I may exist in enantiomeric forms. Therefore, all enantiomers, diastereomers, racemates and mixtures thereof are included within the scope of the invention. The various optical isomers may be isolated by separation of a racemic mixture of the compounds using conventional techniques, for example, fractional crystallisation, or HPLC.

Intermediate compounds may also exist in enantiomeric forms and may be used as purified enantiomers, diastereomers, racemates or mixtures.

The compounds of formula (I), and their pharmaceutically acceptable salts, enantiomers and racemates, are useful because they possess pharmacological activity in animals. In particular, the compounds are active as inhibitors of the enzyme nitric oxide synthase. More particularly, they are inhibitors of the inducible isoform of the enzyme nitric oxide synthase and as such are predicted to be useful in therapy, for example, as anti-inflammatory agents. They may also have utility as inhibitors of the neuronal isoform of the enzyme nitric oxide synthase.

The compounds and their pharmaceutically acceptable salts, enantiomers and racemates are indicated for use in the treatment or prophylaxis of diseases or conditions in which synthesis or oversynthesis of nitric oxide synthase forms a contributory part. In particular, the compounds are indicated for use in the treatment of inflammatory conditions in mammals including man.

Conditions that may be specifically mentioned are:

osteoarthritis, rheumatoid arthritis, rheumatoid spondylitis, gouty arthritis and other arthritic conditions, inflamed joints;

eczema, psoriasis, dermatitis or other inflammatory skin conditions such as sunburn;

inflammatory eye conditions including uveitis, glaucoma and conjunctivitis;

lung disorders in which inflammation is involved, for example, asthma, bronchitis, chronic obstructive pulmonary disease, pigeon fancier's disease, farmer's lung, acute respiratory distress syndrome;

bacteraemia, endotoxaemia (septic shock), aphthous ulcers, gingivitis, pyresis, pain, meningitis and pancreatitis;

conditions of the gastrointestinal tract including inflammatory bowel disease, Crohn's disease, atrophic gastritis, gastritis varialoforme, ulcerative colitis, coeliac disease, regional ileitis, peptic ulceration, irritable bowel syndrome, reflux oesophagitis, damage to the gastrointestinal tract resulting from infections by, for example, *Helicobacter pylori*, or from treatments with non-steroidal anti-inflammatory drugs;

and other conditions associated with inflammation.

The compounds will also be useful in the treatment and alleviation of acute pain or persistent inflammatory pain or neuropathic pain or pain of a central origin.

We are particularly interested in the conditions inflammatory bowel disease, rheumatoid arthritis, osteoarthritis, chronic obstructive pulmonary disease and pain.

The compounds of formula (I) and their pharmaceutically acceptable salts, enantiomers and racemates may also be useful in the treatment or prophylaxis of diseases or conditions in addition to those mentioned above. For example, the compounds may be useful in the treatment of atherosclerosis, cystic fibrosis, hypotension associated with septic and/or toxic shock, in the treatment of dysfunction of the immune system, as an adjuvant to short-term immunosuppression in organ transplant therapy, in the control of onset of diabetes, in the maintenance of pancreatic function in diabetes, in the treatment of vascular complications associated with diabetes and in co-therapy with cytokines, for example TNF or interleukins.

The compounds of formula (I) may also be useful in the treatment of hypoxia, for example in cases of cardiac arrest and stroke, neurodegenerative disorders including nerve degeneration and/or nerve necrosis in disorders such as ischaemia, hypoxia, hypoglycaemia, epilepsy, and in external wounds (such as spinal cord and head injury), hyperbaric oxygen convulsions and toxicity, dementia, for example pre-senile dementia, Alzheimer's disease and AIDS-related dementia, Sydenham's chorea, Parkinson's disease, Tourette's Syndrome, Huntington's disease, Amyotrophic Lateral Sclerosis, Multiple Sclerosis, Korsakoff's disease, imbecility relating to a cerebral vessel disorder, sleeping disorders, schizophrenia, depression, pain, autism, seasonal affective disorder, jet-lag, depression or other symptoms associated with Premenstrual Syndrome (PMS), anxiety and septic shock. Compounds of formula (I) may also be expected to show activity in the prevention and reversal of drug addiction or tolerance such as tolerance to opiates and diazepines, treatment of drug addiction, treatment of migraine and other vascular headaches, neurogenic inflammation, in the treatment of gastrointestinal motility disorders, cancer and in the induction of labour.

We are particularly interested in the conditions stroke, Alzheimer's disease, Parkinson's disease, multiple sclerosis, schizophrenia, migraine, cancer, septic shock and pain.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

For the above mentioned therapeutic indications, the dosage administered will, of course, vary with the compound employed, the mode of administration and the treatment desired. However, in general, satisfactory results are obtained when the compounds are administered at a dosage of the solid form of between 1 mg and 2000 mg per day.

The compounds of formula (I), and pharmaceutically acceptable derivatives thereof, may be used on their own, or in the form of appropriate pharmaceutical compositions in which the compound of derivative is in admixture with a pharmaceutically acceptable adjuvant, diluent or carrier. Administration may be by, but is not limited to, enteral (including oral, sublingual or rectal), intranasal, intravenous, topical or other parenteral routes. Conventional procedures for the selection and preparation of suitable pharmaceutical formulations are described in, for example, "Pharmaceuticals—The Science of Dosage Form Designs", M. E. Aulton, Churchill Livingstone, 1988. The pharmaceutical composition preferably comprises less than 80% and more preferably less than 50% of a compound of formula (I), or a pharmaceutically acceptable salt, enantiomer or racemate thereof.

There is also provided a process for the preparation of such a pharmaceutical composition which comprises mixing the ingredients.

The compounds of formula (I), and pharmaceutically acceptable derivatives thereof, may also be advantageously used in combination with a COX-2 inhibitor. Particularly preferred COX-2 inhibitors are Celecoxib and MK-966. The NOS inhibitor and the COX-2 inhibitor may either be formulated together within the same pharmaceutical composition for administration in a single dosage unit, or each component may be individually formulated such that separate dosages may be administered either simultaneously or sequentially.

The invention is illustrated, but in no way limited, by the following examples:

EXAMPLE 1

4-Chloro-2-[[(1R)-4-(methylamino)-1-phenylbutyl]oxy] benzonitrile ethanedioate a) S-α-(3-Chloropropyl)benzenemethanol)

Borane (24 ml of 1M solution in tetrahydrofuran) was added to a solution of (R)-2-methyl-CBS-oxazaborolidine (2 ml, 1M solution in toluene) in tetrahydrofuran (20 ml) at 0° C. γ-Chlorobutyrophenone (7.38 g) in tetrahydrofuran (45 ml) was added over 30 min and the resultant solution was stirred at 0° C. for 1hand at 20° C. for 18 h. Methanol (25 ml) was added and the mixture was stirred for 15 min. The mixture was evaporated, re-dissolved in methanol and re-concentrated in vacuo. The residue was purified by chromatography on silica eluting with hexane-diethyl ether (4:1) to give the title compound as a colourless oil (6.94 g).

$^1$H NMR 300 MHz (CDCl$_3$) 7.37–7.26 (5H, m), 4.74–4.70 (1H, m), 3.57 (2H, t), 1.96–1.78 (4H, m).

b) 4-Chloro-2-[[(1R)-4-chloro-1-phenylbutyl]oxy] benzonitrile

Diethyl azodicarboxylate (1.86 g) was added dropwise to a solution of triphenylphosphine (2.81 g), 4-chloro-2-hydroxybenzonitrile (1.49 g) and the product from step (a) (1.79 g) in tetrahydrofuran (5 ml) and toluene (60 ml) at 0° C. and stirred at 0° C. for 4hand at 20° C. for 18 h. The solvent was removed in vacuo and the residue was purified by chromatography on silica eluting with hexane-diethyl ether (4:1) to give the title compound as a colourless oil (2.80 g).

$^1$H NMR 300 MHz (CDCl$_3$) 7.46 (1H, d), 7.39–7.31 (5H, m), 6.93 (1H, dd), 6.77 (1H, d), 5.25–5.21 (1H, m), 3.63–3.57 (2H, m), 2.23–1.92 (4H, m).

c) 4-Chloro-2-[[(1R)-4-iodo-1-phenylbutyl]oxy] benzonitrile

A solution of the product from step (b) (2.80 g) and sodium iodide (20 g) in acetone (100 ml) was heated under reflux for 20 h. The mixture was filtered, evaporated, dissolved in water (50 ml) and extracted with ethyl acetate (three times). The organic extracts were washed with water, dried (magnesium sulphate) and evaporated to give the title compound (3.22 g).

$^1$H NMR 300 MHz (CDCl$_3$) 7.46 (1H, d), 7.42–7.30 (5H, m), 6.93 (1H, dd), 6.76 (1H, d), 5.23–5.19 (1H, m), 3.25–3.21 (2H, m), 2.21–1.93 (4H, m).

d) 4-Chloro-2-[[(1R)-4-(methylamino)-1-phenylbutyl]oxy] benzonitrile ethanedioate A solution of the product from step (c) (286 mg) in 40% aqueous methylamine (1 ml) and tetrahydrofuran (10 ml) was stirred for 6 h. The solvent was removed in vacuo and the residue dissolved in water and extracted with ethyl acetate (three times). The combined organic extracts were washed with water, dried (magnesium sulphate) and evaporated to give an oil. To a solution of this amine in methanol (10 ml) was added a solution of oxalic acid (57 mg) in methanol. The solvent was removed in vacuo and the residue triturated with ethyl acetate. The solid was collected and dried to afford the title compound as a white solid (110 mg). M.p. 167–169° C.

MS APCI+ve$^m$/z 315 ([M+H]$^+$)

$^1$H NMR 300 MHz (d$_6$-DMSO) 7.76 (1H, d), 7.44–7.29 (5H, m), 7.22 (1H, d), 7.13 (1H, dd), 5.74 (1H, t), 2.97 (2H, t), 2.52 (3H, s), 2.11–1.86 (2H, m), 1.81–1.60 (2H, m).

EXAMPLE 2

R-γ-(2,5-Dichlorophenoxy)-N-methyl-benzenebutanamine ethanedioate a) 1,4-Dichloro-2-[[(1R)-4-chloro-1-phenylbutyl]oxy] benzene Starting with 2,5-dichlorophenol and the product of Example 1(a), product 2(a) was prepared using the procedure described in Example 1 step (b).

$^1$H NMR 300 MHz (CDCl$_3$) 7.39–7.19 (6H, m), 6.81 (1H, dd), 6.69 (1H, d), 5.19–5.15 (1H, m), 3.63–3.58 (2H, m), 2.19–1.91 (4H, m).

b) 1,4-Dichloro-2-[[(1R)-4-iodo-1-phenylbutyl]oxy] benzene

The product of Example 2(a) was converted into the compound of Example 2(b) by the procedure described in Example 1 step (c).

$^1$H NMR 300 MHz (CDCl$_3$) 7.39–7.23 (6H, m), 6.81 (1H, dd), 6.69 (1H, d), 5.17–5.14 (1H, m), 3.24 (2H, t), 2.17–1.94 (4H, m).

c) R-γ-(2,5-Dichlorophenoxy)-N-methyl-benzenebutanamine ethanedioate

The product of Example 2(b) was converted into the title compound by the procedure described in Example 1 step (d). M.p.167–169° C.

MS APCI+ve $^m$/z 324 ([M+H]$^+$).

$^1$H NMR 300 MHz (d$_6$-DMSO) 7.77 (1H, d), 7.44–7.29 (5H, m), 7.21 (1H, d), 7.13 (1H, dd), 5.74 (1H, t), 2.96 (2H, t), 2.52 (3H, s), 2.11–1.86 (2H, m), 1.81–1.60 (2H, m).

EXAMPLE 3

4-Chloro-2-[[(1R)-1-phenyl-4-(1-pyrrolidinyl)butyl]oxy]-benzonitrile ethanedioate A solution of the product from Example 1 step (c) (200 mg) and pyrrolidine (0.15 ml) in tetrahydrofuran (5 ml) was stirred for 2 days. The solvent was removed in vacuo and the residue dissolved in water and aqueous potassium carbonate and extracted with ethyl acetate (three times). The combined organic extracts were washed with water, dried (Na$_2$SO$_4$) and evaporated to give an oil. To a solution of this amine in isopropanol (3 ml) was added a solution of oxalic acid (44 mg) in methanol (0.3 ml). The crystals that formed on cooling were collected and dried to afford the title compound as a white solid (163 mg). M.p. 157–158° C.

MS APCI+ve $^m$/z 355 ([M+H]$^+$).

$^1$H NMR 300 MHz (d$_6$-DMSO) 7.57 (1H, d), 7.45–7.27 (5H, m), 7.23 (1H, d), 7.13 (1H, dd), 5.72 (1H, dt), 3.28–3.10 (6H, m), 2.08–1.62 (8H, m).

EXAMPLE 4

4-Chloro-2-[[(1R)-4-(4-morpholinyl)-1-phenylbutyl]oxy]-benzonitile ethanedioate

Prepared according to the method of Example 3, using the product of Example 1 step (c) and morpholine. M.p. 155–156° C.

MS APCI+ve $^m$/z 371 ([M+H]$^+$)

$^1$H NMR 300 MHz (d$_6$-DMSO) 7.77 (1H, d), 7.44–7.27 (5H, m), 7.24 (1H, d), 7.13 (1H, dd), 5.71 (1H, dt), 3.78–3.63 (4H, m), 2.87 (6H, s), 2.09–1.04 (4H, m).

EXAMPLE 5

4-Chloro-2-[[(1R)-4-[ethyl(2-hydroxyethyl)amino]-1-phenylbutyl]oxy]-benzonitrile hydrochloride A solution of the product from Example 1 step (c) (200 mg) and 2-(ethylamino)ethanol (163 mg, 0.14 ml) in tetrahydrofuran (5 ml) was stirred for 2 days. The solvent was removed in vacuo and the residue dissolved in water and aqueous potassium carbonate and extracted with ethyl acetate (three times). The combined organic extracts were washed with water, dried (Na2SO4) and evaporated to give an oil. To a solution of this amine in diethyl ether-dichloromethane was added a 1M solution of hydrogen chloride in diethyl ether. The crystals that formed were collected and dried to afford the title compound as a white solid (65 mg). M.p. 141–144° C.

MS APCI+ve $^m$/z 373 ([M+H]$^+$).

$^1$H NMR 300 MHz (d$_6$-DMSO) 9.85 (1H, s), 7.77 (1H, d), 7.46–7.26 (6H, m), 7.13 (1H, dd), 5.78–5.73 (1H, m), 5.34 (1H, s), 3.73 (2H, s), 3.43–3.07 (6H, m), 2.10–1.69 (4H, m), 1.20 (3H, t).

EXAMPLE 6

4-Chloro-2-[[(1R)-1-phenyl-4-[(3-pyridinylmethyl)amino]butyl]oxy]-benzonitrile ethanedioate Prepared according to the method of Example 3, using the product of Example 1 step (c) and 3-pyridinemethanamine. M.p 188–189° C.

MS APCI+ve $^m$/z 392 ([M+H]$^+$).

$^1$H NMR 300 MHz (d$_6$-DMSO) 8.64 (1H, s), 8.57(1H,s), 7.87(1H,d), 7.75–7.73(1H,m), 7.41–7.37 (5H, m), 7.31 (1H, s), 7.24 (1H, s), 7.11(1H,d), 5.71 (1H, s), 4.13 (2H, s), 3.00(2H,s), 2.12–1.62 (4H, m).

EXAMPLE 7

4-Chloro-2-[[(1R)-4-[[2-(1H-imidazol-5-yl)ethyl]amino]-1-methylbutyl]oxy]-benzonitrile ethanedioate Prepared according to the method of Example 3, using the product of Example 1 step (c) and histamine. M.p.182–183° C.

MS APCI+ve $^m$/z 395 ([M+H]$^+$).

$^1$H NMR 300 MHz (d$_6$-DMSO) 7.89 (1H, s), 7.77 (1H, d), 7.45–7.26 (6H, m), 7.12 (1H, dd), 7.04 (1H, s), 5.57 (1H, t), 3.15 (2H, t), 3.03 (2H, t), 2.86 (2H, t), 2.13–1.65 (4H, m).

EXAMPLE 8

4-Chloro-2-[[1R)-4-(1H-imidazol-1-yl)-1-phenylbutyl]oxy]-benzonitrile ethanedioate Prepared according to the method of Example 3, using the product of Example 1 step (c) and imidazole. M.p. 133–134° C.

MS APCI+ve $^m$/z 352 ([M+H]$^+$).

$^1$H NMR 300 MHz (d$_6$-DMSO) 8.40 (1H, s), 7.76 (1H, d), 7.46 (1H, s), 7.41–7.36 (4H, m), 7.32–7.28 (2H, m), 7.23 (1H, d), 7.12 (1H, dd), 5.71 (1H, t), 4.17 (2H, t), 2.00–1.73 (4H, m).

EXAMPLE 9

4-Chloro-2-[[(1R)-4-[(2-hydroxyethyl)amino]-1-phenylbutyl]oxy]-benzonitrile ethanedioate Prepared according to the method of Example 3, using the product of Example 1 step (c) and ethanolamine. M.p. 158–159° C.

MS APCI+ve $^m$/z 345 ([M+H]$^+$).

$^1$H NMR 300 MHz (d$_6$-DMSO) 7.77 (1H, d), 7.44–7.40 (4H, m), 7.37–7.27 (2H, m), 7.13 (1H, dd), 5.76–5.72 (1H, t), 3.64–3.60 (2H, t), 3.01–2.93 (4H, m), 2.10–1.90 (2H, m), 1.87–1.63 (2H, m).

EXAMPLE 10

4-Chloro-2-[[(1R)-4-(cyclopropylamino)-1-phenylbutyl]oxy]-benzonitrile ethanedioate Prepared according to the method of Example 3, using the product of Example 1 step (c) and cyclopropylamine. M.p. 173–174° C.

MS APCI+ve $^m$/z 341 ([M+H]$^+$).

$^1$H NMR 300 MHz (d$_6$-DMSO) 7.77 (1H, d), 7.44–7.37 (4H, m), 7.34–7.27 (2H, m), 7.13 (1H, dd), 5.77–5.73 (1H, t), 3.07–3.02 (2H, t), 2.63–2.57 (1H, m), 2.07–1.89 (2H, m), 1.78–1.61 (2H, m), 0.76–0.65 (4H, m).

EXAMPLE 11

4-Chloro-2-[[(1R)-4-[(3-hydroxypropyl)amino]-1-phenylbutyl]oxy]-benzonitrile ethanedioate Prepared according to the method of Example 3, using the product of Example 1 step (c) and 3-amino-1-propanol. M.p. 111–112° C.

MS APCI+ve $^m$/z 359 ([M+H]$^+$).

$^1$H NMR 300 MHz (d$_6$-DMSO) 7.76 (1H, d), 7.42–7.38 (4H, m), 7.33–7.27 (2H, m), 7.13 (1H, dd), 5.74 (1H, t), 3.48–3.44 (2H, m), 2.98–2.89 (4H, m), 2.04–1.93 (2H, m), 1.80–1.60 (4H, m).

EXAMPLE 12

4-Chloro-2-[[(1R)-4-[[(1R)-2-hydroxy-1-methylethyl]amino]-1-phenylbutyl]oxy]-benzonitrile ethanedioate Prepared according to the method of Example 3, using the product of Example 1 step (c) and (R)-2-amino-1-propanol. M.p. 163–164° C.

MS APCI+ve $^m/z$ 359 ([M+H]$^+$).

$^1$H NMR 300 MHz (d$_6$-DMSO) 7.77 (1H, d), 7.44–7.41 (4H, m), 7.38–7.27 (2H, m), 7.13 (1H, dd), 5.75 (1H, t), 3.63–3.58 (1H, m), 3.47–3.42 (1H, m), 3.18–3.13 (1H, m), 2.98 (2H, t), 2.07–1.87 (2H, m), 1.77–1.64 (2H, m), 1.15 (3H, d).

EXAMPLE 13

4-Chloro-2-[[(1R)-4-[[(1S)-2-hydroxy-1-methylethyl]amino]-1-phenylbutyl]oxy]-benzonitrile ethanedioate Prepared according to the method of Example 3, using the product of Example 1 step (c) and (S)-2-amino-1-propanol. M.p. 186–187° C.

MS APCI+ve $^m/z$ 359 ([M+H]$^+$).

$^1$H NMR 300 MHz (d$_6$-DMSO) 7.77 (1H, d), 7.44–7.41 (4H, m), 7.38–7.27 (2H, m), 7.13 (1H, dd), 5.75 (1H, t), 3.63–3.58 (1H, m), 3.48–3.42 (1H, m), 3.19–3.13 (1H, m), 3.00–2.96 (2H, m), 2.08–1.87 (2H, m), 1.77–1.70 (2H, m), 1.15 (3H, d).

EXAMPLE 14

4-Chloro-2-[4-[[(2-fluoroethyl)amino]-1-phenylbutyl]oxy]-benzonitrile ethanedioate Prepared according to the method of Example 3, using the product of Example 1 step (c) and 2-fluoroethylamine. M.p. 179–180° C.

MS APCI+ve $^m/z$ 347 ([M+H]$^+$).

$^1$H NMR 300 MHz (d$_6$-DMSO) 7.77 (1H, d), 7.44–7.27 (6H, m), 7.13 (1H, dd), 5.74 (1H, t), 4.75 (1H, t), 4.59 (1H, t), 3.28 (1H, t), 3.19 (1H, t), 3.01 (2H, t), 2.07–1.89 (2H, m), 1.80–1.63 (2H, m).

EXAMPLE 15

R-γ-(2,5-Dichlorophenoxy)-4-fluoro-N-methyl benzenebutanamine a) 1,4-Dichloro-2-[[(1R)-4-chloro-1-(4-fluorophenyl)butyl]oxy]-benzene Prepared according to the method of Example 1 step (b) using S-α-(3-chloropropyl)-4-fluorobenzenemethanol and 2,5-dichlorophenol.

$^1$H NMR 300 MHz (CDCl$_3$) 7.36–7.23 (3H, m), 7.09–6.99 (2H, m), 6.82 (1H, dd), 6.67 (1H, d), 5.19–5.14 (1H, m), 3.63 (2H, t), 2.21–1.86 (4H, m).

b) 1,4-Dichloro-2-[[(1R)-4-iodo-1-(4-fluorophenyl)butyl]oxy]-benzene

Prepared according to the method of Example 1 step (c) using the product of step (a) above.

$^1$H NMR 300 MHz (CDCl$_3$) 7.36–7.23 (3H, m), 7.09–6.99 (2H, m), 6.82 (1H, dd), 6.66 (1H, d), 5.16–5.13 (1H, m), 3.24 (2H, t), 2.21–1.93 (4H, m).

c) R-γ-(2,5-Dichlorophenoxy)-4-fluoro-N-methyl benzenebutanamine

Prepared according to the method of Example 1 step (d) using the product of step (b) above to give the title compound. M.p. 160–162° C.

MS APCI+ve $^m/z$ 342 ([M+H]$^+$).

$^1$H NMR 300 MHz (d$_6$-DMSO) 7.48–7.39 (3H, m), 7.22 (2H, t), 7.13 (1H, d), 6.97 (1H, dd), 5.65 (1H, t), 2.94 (2H, t), 2.49 (3H, s), 2.09–1.53 (4H, m).

EXAMPLE 16

S-δ-(2,5-Dichlorophenoxy)-4-fluoro-N-methyl-benzenebutanamine a) 1,4-Dichloro-2-[[(1S)-4-chloro-1-(4-fluorophenyl)butyl]oxy]-benzene Prepared according to the method of Example 1 step (b) using R-α-(3-chloropropyl)-4-fluorobenzenemethanol and 2,5-dichlorophenol.

$^1$H NMR 300 MHz (CDCl$_3$) 7.36–7.23 (3H, m), 7.09–6.99 (2H, m), 6.82 (1H, dd), 6.67 (1H, d), 5.19–5.14 (1H, m), 3.63 (2H, t), 2.21–1.86 (4H, m).

b) 1,4-Dichloro-2-[[(1S)-4-iodo-1-(4-fluorophenyl)butyl]oxy]-benzene

Prepared according to the method of Example 1 step (c) using the product of step (a) above.

$^1$H NMR 300 MHz (CDCl$_3$) 7.35–7.23 (3H, m), 7.09–6.99 (2H, m), 6.82 (1H, dd), 6.66 (1H, d), 5.16–5.13 (1H, m), 3.24 (2H, t), 2.21–1.93 (4H, m).

c) S-δ-(2,5-Dichlorophenoxy)-4-fluoro-N-methyl-benzenebutanamine

Prepared according to the method of Example 1 step (d) using the product of step (b) above to give the title compound. M.p. 158–159° C.

MS APCI+ve $^m/z$ 342 ([M+H]$^+$).

$^1$H NMR 300 MHz (d$_6$-DMSO) 7.48–7.40 (3H, m), 7.22 (2H, t), 7.13 (1H, d), 6.97 (1H, dd), 5.65 (1H, t), 2.94 (2H, t), 2.49 (3H, s), 2.06–1.59 (4H, m).

EXAMPLE 17

R-γ-(2,5-Dichlorophenoxy)-N,4-dimethyl-benzenebutanamine fumarate a) S-α-(3-Chloropropyl)-4-methyl-benzenemethanol 4-Chloro-4'-methylbutyrophenone was converted into the compound of Example 17(a) using the procedure described in Example 1 step (a).

$^1$H NMR 300 MHz (CDCl$_3$) 7.20 (4H, dd), 4.71–4.65 (1H, m), 3.60–3.52 (2H, m), 2.35 (3H, s), 1.98–1.75 (5H, m).

b) 1,4-Dichloro-2-[[(1R)-4-chloro-1-(4-methylphenyl)butyl]oxy]-benzene

Compound 17(b) was prepared from the product of Example 17(a) and 2,5-dichlorophenol, using the procedure described in Example 1 step (b).

$^1$H NMR 300 MHz (CDCl$_3$) 7.26–7.21 (3H, m), 7.15 (2H, d), 6.79 (1H, dd), 6.70 (1H, d), 5.15–5.11 (1H, m), 3.59 (2H, t), 2.33 (3H, s), 2.18–1.91 (4H, m).

c) 1,4-Dichloro-2-[[(1R)-4-iodo-1-(4-methylphenyl)butyl]oxy]-benzene

The product of Example 17(b) was converted into compound 17(c) using the method described in Example 1 step (c).

$^1$H NMR 300 MHz (CDCl$_3$) 7.27–7.17 (5H, m), 6.79 (1H, dd), 6.69 (1H, d), 5.14–5.10 (1H, m), 3.23 (2H, t), 2.33 (3H, s), 2.16–1.92 (4H, m).

d) R-γ-(2,5-Dichlorophenoxy)-N,4-dimethyl-benzenebutanamine fumarate

The product of Example 17(c) (224 mg, 0.5 mmol) was dissolved in tetrahydrofuran (15 ml) and the solution treated with 40% aqueous methylamine (5 ml). After stirring at room temperature for 5 hours, water (30 ml) was added and the mixture extracted with ethyl acetate (3×50 ml). The combined organic extracts were washed with water (2×40 ml), dried (magnesium sulphate) and evaporated in vacuo. The residue was dissolved in methanol (5 ml) and treated with one equivalent of fumaric acid. The mixture was stirred for 10 minutes then evaporated in vacuo. The solid residue was recrystallised from ethyl acetate:ethanol to give the title compound. M.p. 126–130° C.

MS APCI+ve $^m/z$ 338/340 ([M+H]$^+$).

$^1$H NMR 300 MHz (d$_6$-DMSO) 7.42 (1H, d), 7.27 (2H, d), 7.17 (2H, d), 7.09 (1H, s), 6.93 (1H, dd), 6.45 (2H, s), 5.57 (1H, t), 2.89 (2H, t), 2.42 (3H, s), 2.26 (3H, s), 1.97–1.94 (1H, m), 1.88–1.81 (1H, m), 1.78–1.70 (1H, m), 1.65–1.62 (1H, m).

EXAMPLE 18

S-γ-(2,5-Dichlorophenoxy)-N,4-dimethyl-benzenebutanamine fumarate a) R-α-(3-Chloropropyl)-4-methyl-benzenemethanol (S)-2-methyl-CBS-oxazaborolidine was dissolved in tetrahydrofuran (10 ml) and the solution cooled to 0° C. The stirred solution was treated with borane-tetrahydrofuran complex (1M in tetrahydrofuran) (3.4 ml, 3.4 mmol). A solution of 4-chloro-4'-methylbutyrophenone (1.1 g, 5.59 mmol) in tetrahydrofuran (40 ml) was added dropwise over 0.5 hours and the reaction allowed to warm to room temperature overnight. The reaction was quenched with methanol (3.4 ml) and then concentrated in vacuo. Methanol (3.5 ml) was added and the solution was re-concentrated. The residue was passed down a flash silica column, eluting with hexane:diethyl ether (4:1) to give product 18(a) as a colourless oil (1.03 g, 93%, 95% ee).

$^1$H NMR 300 MHz (CDCl$_3$) 7.20 (4H, dd), 4.71–4.65 (1H, m), 3.60–3.52 (2H, m), 2.35 (3H, s), 1.98–1.75 (5H, m).

b) 1,4-Dichloro-2-[[(1S)-4-chloro-1-(4-methylphenyl)butyl]oxy]-benzene

Compound 18 (b) was prepared from the product of Example 18(a) and 2,5-dichlorophenol, using the procedure described in Example 1 step (b).

$^1$H NMR 300 MHz (CDCl$_3$) 7.26–7.13 (5H, m), 6.79 (1H, dd), 6.70 (1H, d), 5.15–5.12 (1H, m), 3.60 (2H, t), 2.33 (3H, s), 2.22–1.89 (4H, m).

c) 1,4-Dichloro-2-[[(1S)-4-iodo-1-(4-methylphenyl)butyl]oxy]-benzene

The compound of Example 18(b) was converted into product 18(c) using the method described in Example 1 step (c).

$^1$H NMR 300 MHz (CDCl$_3$) 7.27–7.14 (5H, m), 6.79 (1H, dd), 6.69 (1H, d), 5.14–5.10 (1H, m), 3.23 (2H, t), 2.33 (3H, s), 2.17–1.92 (4H, m).

d) S-γ-(2,5-Dichlorophenoxy)-N,4-dimethyl-benzenebutanamine fumarate

The product of Example 18(c) was converted into the title compound using the method described in Example 17 step (d). M.p. 126–130° C.

MS APCI+ve$^m$/z 338/340 ([M+H]$^+$).

$^1$H NMR 300 MHz (d$_6$-DMSO) 7.42 (1H, d), 7.27 (2H, d), 7.16 (2H, d), 7.09 (1H, d), 6.94 (1H, dd), 6.42 (2H, s), 5.56 (1H, t), 2.86 (2H, t), 2.46 (3H, s), 2.26 (3H, s), 1.96–1.58 (4H, m).

EXAMPLE 19

δ-(2,5-Dichlorophenoxy)-N-methyl-2-thiophenebutanamine fumarate a) α-(3-Chloropropyl)-2-thiophenemethanol 4-Chloro-1-(2-thienyl)-1-butanone (9.37 g, 50 mmol) was dissolved in ethanol (100 ml) and the solution cooled to 0° C. Sodium borohydride (1.88 g, 50 mmol) was added in one portion and the reaction allowed to warm to room temperature, then stirred for 18 hours. Aqueous 2M hydrochloric acid was added dropwise until the reaction ceased to effervesce. The solvent was removed in vacuo and the residue partitioned between water and ethyl acetate. The layers were separated and the aqueous portion extracted with ethyl acetate (2×100 ml). The combined organic portions were washed with water (50 ml), dried (magnesium sulphate), filtered and evaporated. The residue was passed down a flash silica chromatography column, eluting with hexane: ethyl acetate (4:1) to afford the title compound as a pale straw coloured oil (7.58 g, 79%).

$^1$H NMR 300 MHz (CDCl$_3$) 7.25–7.27 (1H, m), 6.96–7.00 (2H, m), 4.95–5.00 (1H, m) 3.56–3.61 (2H, m), 1.82–2.04 (5H, m).

b) 2-[4-Chloro-1-(2,5-dichlorophenoxy)butyl]thiophene

4-Chloro-1-thiophen-2-yl-butan-1-ol (2.98 g, 15.6 mmol), 2,5-dichlorophenol (2.55 g, 15.6 mmol) and triphenylphosphine (4.91 g,18.7 mmol) were dissolved in anhydrous tetrahydrofuran (80 ml) and the solution cooled to 0° C. Diethyl azodicarboxylate (3.26 g, 18.7 mmol) was added dropwise and the reaction allowed to warm to room temperature, then stirred for 5 hours. The solvent was removed in vacuo and the residue passed down a flash silica chromatography column, eluting with hexane:ethyl acetate (9:1) to give the title compound as a colourless oil (3.0 g, 57%).

$^1$H NMR 300 MHz (CDCl$_3$) 7.25–7.30 (2H, m), 6.99–7.01 (1H, m), 6.94 (1H, m), 6.85 (2H, m), 5.42–5.45 (1H, m), 3.60–3.63 (2H, m), 1.83–2.35 (4H, m).

c) 2-[1-(2,5-Dichlorophenoxy)-4-iodobutyl]thiophene

2-[4-Chloro-1-(2,5-dichlorophenoxy)butyl]thiophene (2.4 g, 7.1 mmol) was dissolved in a saturated solution of sodium iodide in acetone (200 ml) and the reaction refluxed for 20 hours. The reaction mixture was cooled and the solid filtered off. The filtrate was evaporated in vacuo and the residue taken up in water (50 ml). The mixture was extracted with diethyl ether (3×70 ml) and the combined organic portions were washed with water (3×30 ml), dried (magnesium sulphate), filtered and evaporated in vacuo to give the title compound as a pale straw coloured oil (2.91 g, 95%).

$^1$H NMR 300 MHz (CDCl$_3$) 7.24–7.30 (2H, m), 6.95–7.01 (2H, m), 6.85–6.87 (2H, m), 5.40–5.43 (1H, m), 3.22–3.27 (2H, m), 1.91–2.31 (4H, m).

d) γ-(2,5-Dichlorophenoxy)-N-methyl-2-thiophenebutanamine fumarate

2-[1-(2,5-Dichlorophenoxy)-4-iodobutyl]thiophene (407 mg, 0.95 mmol) was dissolved in anhydrous tetrahydrofuran (15 ml) and methylamine (40 wt. % in water) added. The solution was stirred at room temperature for 4.5 hours. The solvent was removed in vacuo and the residue stirred with a sulphonic acid resin in methanol (10 ml). The mixture was filtered and the resin washed with methanol (3×20 ml). The filtrate was discarded and the product liberated with 7N ammonia in methanol. The filtrate was evaporated in vacuo and the residue dissolved in methanol and treated with one equivalent of fumaric acid. The mixture was stirred for 5 minutes then the solvent was removed in vacuo and the solid residue was triturated with ethyl acetate. The solid was filtered off and dried to afford the title compound as a white solid.

$^1$H NMR 300 MHz (CDCl$_3$) 7.48–7.50 (1H, d), 7.41–7.43 (1H, d), 7.33 (1H, d), 7.20 (1H, d), 6.97–7.02 (2H, m), 6.41 (2H, s), 5.91–5.95 (1H, t), 2.85–2.88 (2H, t), 2.45 (3H, s), 2.06–2.14 (1H, m), 1.90–1.97(1H, m), 1.61–1.79 (2H, m).

EXAMPLE 20

2-[(4-Amino-1-phenylbutyl)amino]-4-chloro-benzonitrile fumarate a) [4-(Hydroxyimino)-4-phenylbutyl]carbamic acid, 1,1-dimethylethyl ester A mixture of 1,1-dimethylethyl 4-oxo-4-phenylbutylcarbamate (2.4 g, 9.1 mmol), hydroxylamine hydrochloride (1.27 g, 2 equiv.) and sodium acetate trihydrate (2.5 g, 2 equiv.) was stirred and heated under reflux in 20% aqueous ethanol (60 ml) for 7 h. The reaction mixture was then concentrated and the residue partitioned between saturated aqueous sodium bicarbonate (100 ml) and ethyl acetate (200 ml). The organic extract was dried over magnesium sulphate and concentrated to afford a colourless solid (2.4 g, 95%).

MS APCI+ve$^m$/z 279 ([M+H]$^+$).

$^1$H NMR 300 MHz (d$_6$-DMSO) 11.18 (1H, s), 7.67–7.61 (2H, m), 7.42–7.33 (3H, m), 6.83 (1H, t), 2.95 (2H, q), 2.72–2.53 (2H, m), 1.57 (2H, quintet), 1.37 (9H, s).

b) (4-Amino-4-phenylbutyl)carbamic acid, 1,1-dimethylethyl ester 1,1-Dimethylethyl 4-(hydroxyimino)-4-phenylbutylcarbamate (2.3 g, 8.3 mmol), in absolute ethanol was hydrogenated over 10% palladium on charcoal (0.5 g) at 5 bar pressure for 20 h. The mixture was then filtered and the filtrate concentrated to dryness to afford the title compound as a colourless oil (2.36 g).

MS APCI+ve $^m/z$ 265 ([M+H]$^+$).

$^1$H NMR 300 MHz (CDCl$_3$) 7.36–7.21 (5H, m), 4.57 (1H, br s), 3.89 (1H, t), 3.1 (2H, br q), 1.8–1.3 (15H, m, includes water).

c) 2-[(4-Amino-1-phenylbutyl)amino]-4-chlorobenzonitrile fumarate salt

4-Chloro-2-fluorobenzonitrile (350 mg, 2.25 mmol), the product of Example 20(b) (1 g, 3.78 mmol) and ethyldiisopropylamine (1 ml, 5.78 mmol) were heated under reflux for 3 days. The mixture was concentrated to dryness and purified on silica gel using two columns (diethyl ether/isohexane 2:3, dichloromethane/diethylether 9:1 respectively). The product from the chromatography was then treated with 4N hydrogen chloride in dioxan (10 ml) until LCMS showed that deprotection was complete. The mixture was concentrated to dryness and the residue purified on silica gel (7N ammonia in methanol/dichloromethane 1:9) to afford the title compound free base (90 mg). The amine was converted into the fumarate salt by addition of 1 equivalent of fumaric acid in ethanol (1 ml). The title compound was isolated as a solid (80 mg, 8.5%).

MS APCI+ve $^m/z$ 300/302 ([M+H]$^+$).

$^1$H NMR 400 MHz (d$_6$-DMSO) 7.5–7.21 (6H, m), 6.74–6.35, (3H, m), 6.4, (~1.5H, s), 4.61 (1H, q), 2.81–2.74 (2H, m), 2.07–1.98 (1H, m), 1.81–1.49 (3H, m).

EXAMPLE 21

2-[[1-(3-Aminopropyl)-3-methylbutyl]amino]-4-(trifluoromethyl) benzonitrile fumarate a) 6-Methyl-4-oxoheptylcarbamic acid 1,1-dimethylethyl ester A solution of 1,1-dimethylethyl 2-oxo-1-pyrrolidinecarboxylate (7.5 g, 40.5 mmol) in dry tetrahydrofuran (150 ml) under a nitrogen atmosphere and at –78° C., was treated dropwise with a solution of isobutyl magnesium bromide in diethyl ether (2 molar, 22.5 ml, 45 mmol). The mixture was stirred at –78° C. for 2h then quenched into a saturated aqueous solution of ammonium chloride (100 ml). The products were extracted into ethyl acetate (2×250 ml) and the combined extracts dried over magnesium sulphate. Concentration of the extracts gave an oil which was purified on silica gel using isohexane/diethylether (1:1). The title compound was isolated as a colourless oil (2.3 g, 25%).

$^1$H NMR 300 MHz (CDCl$_3$) 4.6 (1H, br s), 3.11 (2H, q), 2.43 (2H, t), 2.28 (2H, d), 2.13(1H, quintet), 1.44 (9H, s), 0.92 (6H, d).

b) 4-(Hydroxyimino)-6-methylheptylcarbamic acid 1,1-dimethylethyl ester E and Z isomers A solution of 6-methyl-4-oxoheptylcarbamic acid 1,1-dimethylethyl ester (2.3 g, 9.5 mmol) in ethanol (50 ml) was treated with hydroxylamine hydrochloride (722 mg, 1.1 equivalents), sodium acetate trihydrate (1.42 g, 1.1 equivalents) and water (10 ml). The mixture was heated under reflux for 3h then concentrated to dryness. The residue was then extracted into ethyl acetate (2×100 ml), and the combined extracts dried over magnesium sulphate and concentrated. The crude products were purified on silica gel using diethyl ether/isohexane (1:4). Both geometrical isomers were isolated in equal amounts (total 2.1 g, 86%).

$^1$H NMR 400 MHz (CDCl$_3$) (Isomer 1) 7.02 (1H, br s), 4.65 (1H, br s), 3.2–3.1 (2H, br m), 2.25–2.28 (4H, m), 1.99 (1H, septet), 1.75–1.59 (2H, quintet), 1.44 (9H, s), 0.93 (6H, d).

$^1$H NMR 400 MHz (CDCl$_3$) (Isomer 2) 7.81 (1H, br s), 4.85 (1H, br s), 3.2–3.1 (2H, br m), 2.36 (2H, t), 2.04 (2H, d), 1.9 (1H, septet), 1.73–1.6 (2H, m), 1.44 (9H, s), 0.92 (6H, d).

c) 4-Amino-6-methylheptylcarbamic acid 1,1-dimethylethyl ester

A solution of E and Z isomers of 4-(hydroxyimino)-6-methylheptylcarbamic acid 1,1-dimethylethyl ester (2.1 g, 8.13 mmol) in ethanol (75 ml) was hydrogenated at 5 bar pressure over rhodium on alumina (200 mg) for 36 h. The mixture was then filtered and the filtrate concentrated to dryness to afford the title compound in quantitative yield (2 g).

MS APCI+ve $^m/z$ 245 ([M+H]$^+$).

$^1$H NMR 300 MHz (CDCl$_3$) 4.7 (1H, br s), 3.1 (2H, br m), 2.8 (1H, br m), 1.8–1.4 (~16H, m), 0.9 (6H, dd).

d) 4-[[2-Cyano-5-(trifluoromethyl)phenyl]amino]-6-methylheotylcarbamic acid 1,1-dimethylethyl ester A mixture of 2-fluoro-4-trifluoromethylbenzonitrile (0.15 ml, 1.1 mmol) and 4-amino-6-methylheptylcarbamic acid 1,1-dimethylethyl ester (540 mg, 2.2 mmol) in n-butanol (0.5 ml) was heated under reflux for 7 h. The mixture was then concentrated and the residue purified on silica gel eluting with isohexane/diethyl ether (4:1). The title compound was isolated as a viscous oil (250 mg, 55%).

MS APCI+ve $^m/z$ 313 ([M-Boc]$^+$).

$^1$H NMR 300 MHz (CDCl$_3$) 7.41 (1H, d), 6.8–6.78 (3H, m), 4.5–4.3 (3H, m), 3.5 (1H, br m), 3.05 (4H, br m), 2.4–0.8 (m).

e) 2-[[1-(3-Aminopropyl)-3-methylbutyl]amino]-4-(trifluoromethyl)-benzonitrile fumarate 4-[[2-Cyano-5-(trifluoromethyl)phenyl]amino]-6-methylheptylcarbamic acid 1,1-dimethylethyl ester (250 mg, 0.6 mmol) was stirred in a 4M solution of hydrogen chloride in dioxan (15 ml) for 3 h. The mixture was then concentrated to dryness and the residue treated with saturated aqueous sodium carbonate (50 ml). The products were extracted into diethyl ether (100 ml), and the extract dried over magnesium sulphate. Concentration of the extract gave a gum that was purified on silica gel eluting with 10% methanolic ammonia (7N) in dichloromethane. The product from the column was converted into a fumarate salt by addition of one equivalent of fumaric acid in the minimum amount of ethanol. The title compound was isolated as a colourless solid (80 mg, 31%).

MS APCI+ve $^m/z$ 314 ([M+H]$^+$).

$^1$H NMR 300 MHz (d$_6$-DMSO) 7.68 (1H, d), 7.09 (1H, d), 6.87 (1H, d), 6.39 (2H, s), 6.19 (1H, d), 3.78 (1H, br m), 2.7 (2H, m), 1.7–1.4 (6H, m), 1.34–1.25 (1H, m), 0.88 (6H, dd).

EXAMPLE 22

2-[[4-(2,5-Dichlorophenoxy)-4-phenylbutyl]methylamino]ethanol fumarate a) α-(3-Chloropropyl)benzenemethanol A mixture of 4-chloro-1-phenyl-1-butanone (7.35 g) and sodium tetrahydroborate (3.05 g) in tetrahydrofuran (40 ml) was stirred for 36 h. 2M Hydrochloric acid was added and the mixture was extracted three times with ethyl acetate. The combined organic extracts were dried (magnesium sulphate), evaporated and purified by chromatography on silica eluting with petrol-ether to give the sub-title compound as a colourless oil (6.60 g).

$^1$H NMR 300 MHz (CDCl$_3$) 7.41–7.23 (5H, m), 4.70 (1H, t), 3.62–3.49 (2H, m), 1.98–1.76 (5H, m).

b) 1,4-Dichloro-2-(4-chloro-1-phenylbutoxy)benzene

The sub-title compound was prepared according to the method of Example 1 step (b) using the product of step (a) above and 2,4-dichlorophenol.

MS APCI+ve $^m$/z 327 ([M-H]$^+$).

c) 2-[[4-(2,5-Dichlorophenoxy)-4-phenylbutyl]methylamino]ethanol fumarate

A solution of the product from step (b) (0.20 g, 0.61 mmol), 2-(methylamino)ethanol (0.137 g,) 1.83 mmol) and potassium iodide (0.051 g, 0.31 mmol) in N-methylpyrrolidine was heated to 100° C. in a sealed vessel and stirred for 4 h. The reaction was cooled and poured into water (50 ml) and the mixture extracted with ethyl acetate (3×50 ml). The combined organic extracts were washed with water (3×30 ml), dried (magnesium sulphate) and evaporated. The residue was dissolved in methanol and treated with one equivalent of fumaric acid, stirred for ten minutes, then the solvent was removed in vacuo. The solid residue was triturated with ethyl acetate and the white solid obtained filtered off and dried to give the title compound (0.155 g).

MS APCI+ve $^m$/z 369/371 ([M+H]$^+$).

$^1$H NMR 400 MHz (d$_6$-DMSO) 7.44–7.28 (5H, m), 7.27–7.26 (1H, m), 7.09 (1H, s), 6.94 (1H, dd), 6.54 (1H, s), 5.59 (1H, t), 3.52 (2H, t), 2.57–2.61 (4H, m), 2.30 (3H, s), 2.01–1.92 (1H, m), 1.87–1.78 (1H, m), 1.67–1.50 (2H, m).

EXAMPLE 23

1-[4-(2,5-Dichlorophenoxy)-4-phenylbutyl]-4-piperidinol fumarate

A solution of the product from Example 22 step (b) (0.20 g, 0.61 mmol), 4-hydroxypiperidine (0.185 g, 1.83 mmol) and potassium iodide (0.051 g, 0.31 mmol) in N-methylpyrrolidine was heated to 100° C. in a sealed vessel and stirred for 4 h. The reaction was cooled, poured into water (50 ml) and the mixture extracted with ethyl acetate (3×50 ml). The combined organic extracts were washed with water (3×30 ml), dried (magnesium sulphate) and evaporated. The residue was dissolved in methanol and treated with one equivalent of fumaric acid. This was stirred for ten minutes then the solvent was removed in vacuo. The solid residue was triturated with ethyl acetate and the white solid obtained filtered off and dried to give the title compound (0.140 g, 45%).

MS APCI+ve $^m$/z 394 ([M+H]$^+$).

$^1$H NMR 300 MHz (d$_6$-DMSO) 7.44–7.26 (6H, m), 7.08 (1H, s), 6.94 (1H, d), 6.53 (2H, s), 5.58 (1H, m), 3.57–3.42 (1H, m), 2.84–2.72 (2H, m), 2.36–2.18 (2H, m), 2.03–1.29 (10H, m).

EXAMPLE 24

1-[4-(2,5-Dichlorophenoxy)-4-phenylbutyl]piperazine fumarate a) 1,1-Dimethylethy 4-[4-(2,5-dichlorophenoxy)-4-phenylbutyl]-1-piperazinecarboxylate A solution of the product from Example 22 step (b) (0.20 g, 0.61 mmol), 1-tert-butoxycarbonylpiperazine (0.34 g, 1.83 mmol) and potassium iodide (0.051 mg, 0.31 mmol) in N-methylpyrrolidine was heated to 100° C. in a sealed vessel and stirred for 4 h. The reaction was cooled and poured into water (50 ml) and the mixture extracted with ethyl acetate (3×50 ml). The combined organic extracts were washed with water (3×30 ml), dried (magnesium sulphate) and evaporated to leave an oily residue (0.20 g, 70%).

MS APCI+ve $^m$/z 380/382 ([M-Boc]$^+$).

b) 1-[4-(2,5-Dichlorophenoxy)-4-phenylbutyl]piperazine fumarate

The product from step (a) (0.20 g, 0.42 mmol) was dissolved in 4M hydrogen chloride in dioxan (10 ml) and stirred for 3hat room temperature. The solvent was evaporated and the residue partitioned between ethyl acetate (50 ml) and aqueous saturated sodium bicarbonate solution (50 ml). The layers were separated and the aqueous portion was extracted with ethyl acetate (2×50 ml). The combined organic portions were washed with water (3×30 ml), dried (magnesium sulphate) and evaporated. The residue was dissolved in methanol and treated with one equivalent of fumaric acid, stirred for ten minutes and then the solvent was removed in vacuo. The solid residue was triturated with ethyl acetate and the white solid obtained filtered off and dried to give the title compound (0.10 g, 49%)., MS APCI+ve $^m$/z 379/381 ([M+H]$^+$).

$^1$H NMR 400 MHz (d$_6$-DMSO) 7.61–7.57 (1H, m), 7.44–7.35 (4H, m), 7.32–7.27 (1H, m), 7.08 (1H, d), 6.94 (1H, dd), 6.46 (2H, s), 5.56 (1H, t), 3.04–2.94 (4H, m), 2.51–2.45 (4H, m), 2.33 (2H, t), 2.02–1.93 (1H, m), 1.85–1.78 (1H, m), 1.59–1.43 (2H, m).

EXAMPLE 25

1-[4-(2,5-Dichlorophenoxy)-4-(2-thienyl)butyl]-4-methylpiperazine difumarate

The product from Example 19 step (c) (0.35 g, 0.83 mmol) was dissolved in anhydrous tetrahydrofuran (10 ml) and N-methylpiperazine (0.25 g, 2.49 mmol) added and stirred at room temperature for, 18 h. The precipitated white solid was filtered off and discarded. The filtrate was evaporated and the residue dissolved in methanol and placed on a CC SCX resin. After washing with methanol (150 ml), the product was liberated with 7N ammonia in methanol (100 ml). The solvents were evaporated and the residue dissolved in methanol, treated with one equivalent of fumaric acid, and stirred for ten minutes. The solvent was removed in vacuo and the solid residue recrystallised from hot isopropanol to afford the title compound (0.13 g, 30%).

MS APCI+ve $^m$/z 399/401 ([M+H]$^+$).

$^1$H NMR 400 MHz (d$_6$-DMSO) 7.49 (1H, d), 7.42 (1H, d), 7.30 (1H, d), 7.19 (1H, d), 7.02–6.92 (2H, m), 6.58 (4H, s), 5.90 (1H, t), 2.67–2.33 (8H, m), 2.30 (3H, s), 2.22–2.08 (1H, m), 2.06–2.03 (1H, m), 1.92–1.82 (1H, m), 1.80–1.68 (1H, m), 1.57–1.42 (2H, m).

EXAMPLE 26

4-Chloro-2-[4-(methylamino)-1-(3-thienyl)butoxy]-benzonitrile oxalate a) 1-(3-Thienyl)-1,4-butanediol 3-Chloropropanol (6.77 ml, 81 mmol) was dissolved in anhydrous tetrahydrofuran (100 ml) and the solution cooled to 0° C. i-Propyl magnesium chloride, 2M solution, (40.5 ml, 81 mmol) was added dropwise, keeping the temperature at 0° C. When the addition was complete the reaction was allowed to warm to room temperature. Magnesium (2.96 g, 122 mmol) was added in one portion, followed by dibromoethane (0.1 ml). The reaction was heated and gently refluxed for 3 h, adding more dibromoethane (0.1 ml) at 1 and 2 h. The reaction was cooled and left to stand overnight. The resultant Grignard solution was titrated and had a concentration of 0.4M. The Grignard reagent prepared above (30 ml, 12 mmol) was syringed into a nitrogen flushed 3-necked flask, cooled to 0° C. and treated dropwise with 3-thiophene carboxaldehyde (1.12 g, 10 mmol) in tetrahydrofuran (10 ml). The reaction was allowed to warm to room temperature slowly and then stirred for a further 18 h. Saturated aqueous ammonium chloride (20 ml) was added and the mixture extracted with ethyl acetate (3×75 ml). The combined organic extracts were washed with water (20 ml), dried (magnesium sulphate) and evaporated to afford the title compound as a colourless oil (1.52 g, 88%).

$^1$H NMR 300 MHz (CDCl$_3$) 7.32–7.29 (1H, m), 7.20 (1H, d), 7.08 (1H, dd), 4.84 (1H, t), 3.72–3.66 (2H, m), 2.59 (1H, bs), 2.00 (1H, bs), 1.95–1.86 (2H, m), 1.75–1.65 (2H, m).

b) α-[3-[[(1,1-Dimethylethyl)dimethylsilyl]oxy]propyl]-3-thiophenemethanol

The product from step (a) (0.79 g, 4.58 mmol) was dissolved in dimethylformamide (5 ml) and triethylamine (1.28 ml, 9.16 mmol) and 4-dimethylaminopyridine (0.02 g) added. The solution was cooled to 0° C. and t-butyldimethylsilylchloride (0.655 g, 4.35 mmol), as a solution in dimethylformamide (35 ml), was added dropwise over half an hour. The reaction was stirred at 0° C. for 2 h, then allowed to warm to room temperature slowly. After stirring for a further 18 h, water (50 ml) was added and the reaction extracted with ethyl acetate (3×70 ml). The combined extracts were washed with water (3×20 ml), dried (magnesium sulphate) and evaporated. The residue was chromatographed on flash silica, eluting with hexane:ethyl acetate (4:1) to give the title compound as a colourless oil (1.164 g, 89%).

$^1$H NMR 300 MHz (CDCl$_3$) 7.23–7.19 (1H, m), 7.13–7.11 (1H, m), 7.00 (1H, d), 4.76–4.71 (1H, m), 3.61 (2H, t), 2.99 (1H, d), 1.88–1.77 (2H, m), 1.63–1.56 (2H, m), 0.84 (9H, s), 0.02 (6H, s).

c) 4-Chloro-2-[4-[[(1,1-dimethylethyl)dimethylsilyl]oxy]-1-(3-thienyl)butoxy]benzonitrile The product from step (b) (1.164 g, 4.06 mmol) was dissolved in anhydrous tetrahydrofuran (80 ml) and 2-hydroxy-4-chlorobenzonitrile (624 mg, 4.06 mmol) and triphenylphosphine (1.172 g, 4.47 mmol) added. The solution was cooled to 0° C. and diethyl azodicarboxylate (0.71 ml, 4.47 mmol) added dropwise. The reaction was allowed to warm to room temperature and stirred for a further 18 h. The reaction was concentrated in vacuo and the residue chromatographed on flash silica, eluting with hexane:ethyl acetate (4:1), to afford the title compound as a colourless oil (1.12 g, 65%).

$^1$H NMR 300 MHz (CDCl$_3$) 7.45 (1H, d), 7.34–7.26 (1H, m), 7.25–7.23 (1H, m), 7.09 (1H, d), 6.93 (1H, dd), 6.87 (1H, d), 5.40 (1H, t), 3.69–3.64 (2H, m), 2.13–2.01 (2H, m), 1.71–1.62 (2H, m), 0.88 (9H, s), 0.04 (6H, s).

d) 4-Chloro-2-[4-hydroxy-1-(3-thienyl)butoxy]benzonitrile

The product from step (c) (1.12 g, 2.65 mmol) was dissolved in ethanol (60 ml) and pyridinium p-toluenesulphonate (0.067 g, 0.27 mmol) added. The reaction was heated to 55° C. and stirred for 18 h. The reaction was cooled and the solvent removed in vacuo. The residue was dissolved in ethyl acetate (180 ml) and the organic layer washed with aqueous saturated sodium bicarbonate solution (2×30 ml), water (2×30 ml) and brine (20 ml). After drying over magnesium sulphate, the solution was evaporated in vacuo to give the title compound as a colourless oil (0.72 g, 88%).

MS APCI+ve $^m$/z 309/311 ([M+H]$^+$).

$^1$H NMR 400 MHz (CDCl$_3$) 7.43 (1H, d), 7.35–7.30 (1H, m), 7.25 (1H, d), 7.06 (1H, d), 6.91 (1H, d), 6.87 (1H, s), 5.41–5.38 (1H, m), 3.73–3.63 (2H, m), 2.21–1.59 (4H, m).

e) 4-Chloro-2-[4-(methylamino)-1-(3-thienyl)butoxy]benzonitrile oxalate

The product from step (d) (0.38 g, 1.23 mmol) was dissolved in anhydrous tetrahydrofuran (100 ml) and triphenylphosphine (1.062 g, 4.05 mmol) added. The solution was cooled to 0° C. and N-iodosuccinimide (0.912 g, 4.05 mmol) added. The reaction was allowed to warm to room temperature overnight, whilst stirring. Methylamine, as a 40% aqueous solution, (5 ml) was added and the reaction stirred for 24 h. Saturated aqueous sodium bicarbonate solution (40 ml) was added and the mixture extracted with ethyl acetate (3×70 ml). The combined extracts were washed with water (20 ml), dried (magnesium sulphate) and evaporated in vacuo. The residue was dissolved in methanol and applied to CC SCX resin. The resin was washed with methanol (200 ml) and the product liberated with 7N ammonia in methanol (100 ml). The solvent was removed in vacuo and the product converted into an oxalate salt and recrystallised from ethanol to give the title compound as a white solid (0.185 g, 37%).

MS APCI+ve $^m$/z 321/323 ([M+H]$^+$).

$^1$H NMR 300 MHz (d$_6$-DMSO) 7.76 (1H, d), 7.58–7.56 (2H, m), 7.37–7.36 (1H, d), 7.16–7.12 (2H, m), 5.81 (1H, t), 2.95 (2H, t), 2.52 (3H, s), 2.13–1.89 (2H, m), 1.78–1.57 (2H, m).

EXAMPLE 27

4-Chloro-2-[1-(3-furanyl)-4-(methylamino)butoxy]benzonitrile oxalate a) 1-(3-Furanyl)-1,4-butanediol The Grignard reagent prepared in Example 26 step (a) (0.7M, 28 ml, 19.6 mmol) and furan-3-carboxaldehyde (1.92 g, 20 mmol) in anhydrous tetrahydrofuran (15 ml) were used to prepare the title compound, using the procedure described in Example 26 step (a). The product was a colourless oil (2.42 g, 79%).

$^1$H NMR 300 MHz (CDCl$_3$) 7.39 (2H, s), 6.40 (1H, s), 4.72 (1H, t), 3.74–3.62 (2H, m), 2.58 (1H, s), 2.10 (1H, s), 1.91–1.78 (2H, m), 1.75–1.58 (2H, m).

b) α-[3-[[(1,1-Dimethylethyl)dimethylsilyl]oxy]propyl]-3-furanmethanol

The product of step (a) (2.41 g, 15.4 mmol), t-butyldimethylsilylchloride (2.291 g, 15.2 mmol), triethylamine (4.3 ml, 30.8 mmol), 4-dimethylaminopyridine (0.02 g) and dimethylformamide (70 ml) were used to prepare the title compound, using the procedure described in Example 26 step (b). The product was a colourless oil (2.65 g, 64%).

$^1$H NMR 300 MHz (CDCl$_3$) 7.31 (2H, s), 6.32 (1H, s), 4.65–4.59 (1H, m), 3.65–3.58 (2H, t), 2.88 (1H, d), 1.85–1.75 (2H, m), 1.63–1.54 (2H, m), 0.83 (9H, s), 0.01 (6H, s).

c) 4-Chloro-2-[4-[[(1,1-dimethylethyl)dimethylsilyl]oxy]-1-(3-furanyl)butoxy]benzonitrile The product from step (b) (1.33 g, 4.9 mmol), 4-chloro-2-hydroxybenzonitrile (0.753 g, 4.9 mmol), triphenylphosphine (1.35 g, 5.15 mmol), diethyl azodicarboxylate (0.89 g, 5.15 mmol) and tetrahydrofuran (50 ml) were used to prepare the title compound via the method described in Example 26 step (c). The product was a colourless oil (1.27 g, 64%).

$^1$H NMR 300 MHz (CDCl$_3$) 7.47–7.39 (3H, m), 6.97–6.94 (2H, m), 6.42 (1H, s), 5.32 (1H, t), 3.67 (2H, t), 2.15–1.96 (2H, m), 1.73–1.63 (2H, m), 0.88 (9H, s), 0.04 (6H, s).

d) 4-Chloro-2-[1-(3-furanyl)-4-hydroxybutoxy]benzonitrile

The product of step (c) (1.27 g, 3.13 mmol), pyridinium-p-toluene sulphonate (0.079 g, 0.31 mmol) and ethanol (100 ml) were used to prepare the title compound using the procedure described in Example 26 step (d). Yield (0.87 g, 95%).

$^1$H NMR 300 MHz (CDCl$_3$) 7.48–7.41 (3H, m), 6.99–6.95 (2H, m), 6.43 (1H, s), 5.31 (1H, t), 3.73 (2H, t), 2.19–2.00 (2H, m), 1.81–1.69 (2H, m), 1.42 (1H, s).

e) 4-Chloro-2-[1-(3-furanyl)-4-(methylamino)butoxy]benzonitrile oxalate

Following the procedure described in Example 26 step (e), the product from step (d) above (0.83 g, 2.84 mmol), triphenylphosphine (1.64 g, 6.24 mmol), N-iodosuccinimide (1.4 g, 6.24 mmol), and tetrahydrofuran (60 ml) were used to prepare the iodo intermediate as a tetrahydrofuran solution. A portion of the solution (30 ml, 1.42 mmol) was treated with methylamine gas being bubbled through. The procedure of Example 26 step (e) was then followed to give the title compound as a white solid (0.35 g, 62%).

MS APCI+ve $^m/z$ 305/307 ([M+H]$^+$).

$^1$H NMR 300MHz (d$_6$-DMSO) 7.79–7.74 (2H, m), 7.67 (1H, s), 7.44 (1H, s), 7.16 (1H, d), 6.51 (1H, d), 5.70 (1H, t), 2.96 (2H, t), 2.53 (3H, s), 2.12–1.87 (2H, m), 1.78–1.57 (2H, m).

EXAMPLE 28

2-[4-Amino-1-(3-furanyl)butoxy]-4-chlorobenzonitrile oxalate

To a tetrahydrofuran solution of the iodo intermediate from Example 27 step (e) (30 ml, 1.42 mmol), was added dropwise a solution of sodium azide (0.28 g, 4.26 mmol) in dimethyl sulphoxide (5 ml). The reaction was then stirred for 22hat room temperature. The solution was then treated with triphenylphosphine (1.12 g, 4.26 mmol) and water (5 ml) and stirred for 24hat room temperature. Aqueous saturated sodium bicarbonate solution (30 ml) was added and the mixture extracted with ethyl acetate (3×70 ml). The combined extracts were washed with water (2×30 ml), dried (sodium sulphate) and evaporated. The residue was dissolved in methanol, applied to a CC SCX resin, washed with methanol (200 ml) and then eluted with 7N ammonia in methanol (100 ml). The solvent was removed in vacuo and the residue-chromatographed on flash silica, eluting with 7% 7N ammonia in methanol in dichloromethane. The product was dissolved in methanol, treated with one equivalent of oxalic acid, stirred for ten minutes and then the solvent was removed in vacuo. The solid residue was recrystallised from isopropanol to give the title compound as a white solid (0.26 g, 47%).

MS APCI+ve $^m/z$ 291/293 ([M+H]$^+$).

$^1$H NMR 400 MHz (d$_6$-DMSO) 7.79–7.74 (2H, m), 7.66 (1H, s), 7.46 (1H, s), 7.15 (1H, d), 6.51 (1H, s), 5.70 (1H, t), 2.86 (2H, t), 2.11–1.88 (2H, m), 1.74–1.55 (2H, m).

EXAMPLE 29

4-Chloro-2-[1-(2-furanyl)-4-(methylamino)butoxy]benzonitrile oxalate a) 1-(2-Furanyl)-1,4-butanediol The Grignard reagent prepared in Example 26 step (a) (0.7 M, 28 ml, 19.6 mmol), and furan-2-carboxaldehyde (1.92 g, 20 mmol) in anhydrous tetrahydrofuran (15 ml) were used to prepare the sub-title compound, using the procedure described in Example 26 step (a). The product was a colourless oil (2.69 g, 88%).

$^1$H NMR 300 MHz (CDCl$_3$) 7.37 (1H, s), 6.33 (1H, dd), 6.24 (1H, d), 4.75 (1H, t), 3.71 (2H, t), 2.68 (1H, s), 2.07–1.88 (3H, m), 1.79–1.68 (2H, m).

b) α-[3-[[(1,1-Dimethylethyl)dimethylsilyl]oxy]propyl]-2-furanmethanol

The product of step (a) (2.684 g, 17.2 mmol), t-butyldimethylsilylchloride (2.56 g, 17.2 mmol), triethylamine (4.8 ml, 34.4 mmol), 4-dimethylaminopyridine (0.02 g) and dimethylformamide (70 ml) were used to prepare the sub-title compound, using the procedure described in Example 26 step (b). The product was a colourless oil (3.04 g, 66%).

$^1$H NMR 300 MHz (CDCl$_3$) 7.28 (1H, d), 6.26–6.24 (1H, m), 6.16 (1H, d), 4.66–4.46 (1H, m), 3.61 (2H, t), 2.99 (1H, d), 1.93–1.84 (2H, m), 1.61–1.56 (2H, m), 0.83 (9H, s), 0.00 (6H, s).

c) 4-Chloro-2-[4-[[(1,1-dimethylethyl)dimethylsilyl]oxy]-1-(2-furanyl)butoxy]benzonitrile The product from step (b) (1.52 g, 5.6 mmol), 4-chloro-2-hydroxybenzonitrile (0.86 g, 5.6 mmol), triphenylphosphine (1.54 g, 5.9 mmol), diethyl azodicarboxylate (1.02 g, 5.9 mmol) and tetrahydrofuran (50 ml) were used to prepare the sub-title compound using the method described in Example 26 step (c). The product was a colourless oil (1.32 g, 58%).

$^1$H NMR 300 MHz (CDCl$_3$) 7.46–7.40 (2H, m), 7.04 (1H, s), 6.97 (1H, dd), 6.35 (2H, s), 5.32 (1H, t), 3.71–3.65 (2H, m), 2.26–2.11 (2H, m), 1.74–1.64 (2H, m), 0.88 (9H, s), 0.04 (6H, s).

d) 4-Chloro-2-[1-(2-furanyl)-4-hydroxybutoxy]benzonitrile

The product of step (c) (1.32 g, 3.25 mmol), pyridinium-p-toluene sulphonate (0.082 g, 0.33 mmol) and ethanol (100 ml) were used to prepare the sub-title compound using the procedure described in Example 26 step (d). Yield (0.10 g, 10%).

$^1$H NMR 300 MHz (CDCl$_3$) 7.45 (1H, d), 7.41 (1H, s), 7.04 (1H, s), 6.98 (1H, d), 6.38–6.33 (2H, m), 5.31 (1H, t), 3.75–3.71 (2H, t), 2.31–2.17 (2H, m), 1.80–1.66 (2H, m), 1.57 (1H, bs).

e) 4-Chloro-2-[1-(2-furanyl)-4-(methylamino)butoxy]benzonitrile oxalate

The title compound was prepared by the procedure described for Example 26 step (e) using the product of step (d) above (0.10 g, 0.34 mmol), triphenylphosphine (0.18 g, 0.68 mmol), N-iodosuccinimide (0.154 g, 0.68 mmol), tetrahydrofuran (25 ml) and 40% aqueous methylamine (5 ml). Yield (0.021 g, 16%).

MS APCI+ve $^m/z$ 305/307 ([M+H]$^+$).

$^1$H NMR 300 MHz (d$_6$-DMSO) 7.73 (1H, d), 7.69 (1H, s), 7.55 (1H, s), 7.18 (1H, d), 6.62 (1H, d), 6.47–6.44 (1H, m), 5.80 (1H, t), 2.96 (2H, t), 2.53 (3H, s), 2.19–2.02 (2H, m), 1.77–1.61 (2H, m).

EXAMPLE 30

2-[[(1R)-4-Amino-1-(1-methyl-1H-imidazol-2-yl)butyl]oxy]-4-chloro-5-fluorobenzonitrile hydrochloride a) [4-(1-Methyl-1H-imidazol-2-yl)-4-oxobutyl]carbamic acid 1,1-dimethylethyl ester N-methylimidazole (0.83 g, 10.1 mmol) was dissolved in anhydrous tetrahydrofuran (30 ml) and the solution cooled to −70° C. n-Butyllithium (2.29M, 3.48 ml, 10.1 mmol) was added dropwise and the solution stirred for 0.5hat −70° C. 1,1-Dimethylethyl [4-(methoxymethylamino)-4-oxobutyl]-carbamate (1.24 g, 5.03 mmol) as a solution in tetrahydrofuran (50 ml) was added dropwise and the resultant solution stirred at −70° C. for 1 h. The cooling bath was removed and the reaction mixture allowed to warm to 0° C. The reaction was quenched with saturated aqueous ammonium chloride solution (30 ml) and extracted with ethyl acetate (3×70 ml). The combined extracts were washed with water (2×20 ml), dried (magnesium sulphate) and evaporated. The residue was eluted down a flash chromatography column eluting with hexane:ethyl acetate (3:1) to afford the sub-title compound as a pale straw-coloured oil (0.82 g, 61%);

$^1$H NMR 300 MHz (CDCl$_3$) 7.12 (1H, s), 7.02 (1H, s), 4.80 (1H, s), 4.00 (3H, s), 3.23–3.13 (4H, m), 1.96–1.86 (2H, m), 1.43 (9H, s).

b) [(4R)-4-Hydroxy-4-(1-methyl-1H-imidazol-2-yl)butyl]carbamic acid 1,1-dimethylethyl ester The product of step (a) (0.60 g, 2.24 mmol) was reacted with (3aS)-tetrahydro-1-methyl-3,3-diphenyl-3H-pyrrolo[1,2-c][1,3,2]oxazaborole (1M in toluene, 0.22 ml) and borane-:tetrahydrofuran complex (1M, 1.5 ml, 1.5 mmol) in tetrahydrofuran (40 ml) using the procedure described in Example 1 step (a) to give the sub-title compound as a colourless oil (0.25 g, 42%).

MS APCI+ve $^m/z$ 270 ([M+H]$^+$).

c) 1,1-Dimethylethyl [(4R)-4-(5-chloro-2-cyano-4-fluorophenoxy)-4-(1-methyl-1H-imidazol-2-yl)butyl]-carbamate The product of step (b) (0.24 g, 0.9 mmol) was dissolved in dry dimethylformamide (20 ml), sodium hydride (60% dispersion in oil, 0.04 g, 0.95 mmol) was added in one portion and the mixture stirred at room temperature for 0.5 h. 4-Chloro-2,5-difluorobenzonitrile (0.16 g, 0.9 mmol), as a solution in dry dimethylformamide (5 ml), was added dropwise and the reaction stirred for 18h at room temperature. Water (25 ml) was added and the reaction mixture extracted with ethyl acetate (3×60 ml). The combined organic extracts were washed with water (2×20 ml), dried (magnesium sulphate) and evaporated. The residue was eluted down a flash chromatography column using hexane-:ethyl acetate (1:3) as eluent to give the sub-title compound as a white crystalline solid (0.34 g, 88%).

$^1$H NMR 300 MHz (CDCl$_3$) δ7.40 (1H, d), 7.34 (1H, d), 7.11 (1H, d), 6.82 (1H, d), 6.13 (1H, q), 4.65 (1H, bs), 3.87 (3H, s), 3.22 (2H, m), 2.27–2.21 (1H, m), 2.13–2.08 (1H, m), 1.86–1.79 (1H, m), 1.68–1.63 (1H, m), 1.43 (9H, s).

d) 2-[[(1R)-4-Amino-1-(1-methyl-1H-imidazol-2-yl)butyl]oxy]-4-chloro-5-fluoro-benzonitrile hydrochloride The product of step (c) (0.33 g, 0.78 mmol) was dissolved in 4M hydrochloric acid in dioxan (10 ml) and stirred for 10 minutes. The solvent was removed in vacuo and the solid residue triturated with ethyl acetate. The white solid was filtered off and dried under high vacuum to give the title compound (0.22 g, 70%).

MS APCI+ve $^m$/z 323 ([M+H]$^+$).

$^1$H NMR 300 MHz (d$_6$-DMSO) δ8.12 (1H, d), 8.08 (3H, bs), 7.82–7.79 (1H, m), 7.75 (1H, s), 7.67 (1H, s), 6.31–6.22 (1H, m), 3.95 (3H, s), 2.89–2.74 (2H, m), 2.32–2.25 (2H, m), 1.76–1.56 (2H, m).

EXAMPLE 31

4-Chloro-2-[4-(methylamino)-1-(2-pyridinyl)butoxy]benzonitrile oxalate a) 1-(2-Pyridinyl)-1,4-butanediol i-Propyl magnesium chloride (11.6 ml, 2M in tetrahydrofuran) was added dropwise to a solution of 3-chloropropanol (2.1 g) in tetrahydrofuran (20 ml) at 0° C. Magnesium turnings (0.8 g) and 1,2-dibromoethane (1 drop) were added and the mixture was refluxed for 5h and then added at 0° C. to a solution of pyridine-2-carboxaldehyde (1.3 g) in tetrahydrofuran (10 ml). The mixture was quenched with aqueous ammonium chloride and basified to pH 9 with aqueous potassium carbonate. Extraction with ethyl acetate and then extraction of the residual inorganics with methanol, followed by evaporation and purification by chromatography on silica eluting with dichloromethane—2M ammonia gave the sub-title compound as a brown oil (1.1 g).

MS APCI+ve $^m$/z 168 ([M+H]$^+$).

b) α-[3-[[(1,1-Dimethylethyl)dimethylsilyl]oxy]propyl]-2-pyridinemethanol

A solution of the product from step (a) (0.67 g), tert-butylchlorodimethylsilane (0.6 g), triethylamine (0.56 ml) and dimethylaminopyridine (0.01 g) in dimethylformamide (5 ml) was stirred for 2h at 0° C. and at 20° C. for 16 h. Water was added and the mixture was extracted with ethyl acetate (three times). The combined organic extracts were washed with water, dried (sodium sulphate), evaporated and purified by chromatography on silica eluting with petrol-acetone to give the sub-title compound as a colourless oil (0.58 g).

MS APCI+ve $^m$/z 282 ([M+H]$^+$).

c) 4-Chloro-2-[[4-[[(1,1-dimethylethyl)dimethylsilyl]oxy]-1-(2-pyridinyl)butoxy]benzonitrile The sub-title compound was prepared according to the method of Example 1 step (b) using the product of step (b) above and 4-chloro-2-hydroxybenzonitrile.

MS APCI+ve $^m$/z 417 ([M+H]$^+$).

d) 4-Chloro-2-[4-hydroxy-1-(2-pyridinyl)butoxy]benzonitrile

A solution of the sub-title compound from step (c) (0.6 g) and p-toluenesulphonic acid (20 mg) in methanol was stirred for 24 h. 2M Potassium carbonate solution (0.1 ml) was added and the solvent was removed in vacuo. Aqueous sodium hydrogen carbonate was added and the mixture was extracted with dichloromethane three times. The combined organic extracts were washed with water, dried (sodium sulphate) and evaporated to give an oil. Purification by chromatography on silica eluting with petrol-acetone gave the sub-title compound as a colourless oil (0.38 g).

MS APCI+ve $^m$/z 303 ([M+H]$^+$).

e) 4-Chloro-2-[4-(methylamino)-1-(2-pyridinyl)butoxy]benzonitrile oxalate

A solution of the alcohol from step (d) (0.17 g), tosyl chloride (0.12 g), triethylamine (0.16 ml) and dimethylaminopyridine (5 mg) in tetrahydrofuran (4 ml) was stirred for 12 h at 0° C. and at 20° C. for 24 h. 40% Aqueous methylamine solution (3 ml) was added and the mixture was stirred for 18 h. The solvent was removed in vacuo and residue dissolved in water and extracted with dichloromethane three times. The combined organic extracts were washed with water, dried (magnesium sulphate) and evaporated to give an oil. Purification by chromatography on silica eluting with dichloromethane—3M ammonia in methanol gave a pale yellow gum (75 mg). To a solution of this amine in 2-propanol (3 ml) was added a solution of oxalic acid (23 mg) in hot methanol (0.3 ml). The crystals that formed on cooling were collected and dried to afford the title compound as a white solid (76 mg). M.p. 170–171° C.

MS APCI+ve $^m$/z 316 ([M+H]$^+$).

$^1$H NMR 400 MHz (d$_6$-DMSO) 8.60 (d, 1H), 7.87 (td, 1H), 7.78 (d, 2H), 7.47 (d, 1H), 7.38 (dd, 1H), 7.16 (dd, 2H), 5.66 (t, 1H), 2.95 (t, 2H), 2.57 (s, 3H), 2.16–1.97 (m, 2H), 1.80–1.62 (m, 2H)

EXAMPLE 32

4-Chloro-5-fluoro-2-[4-(methylamino)-1-(2-pyridinyl)butoxy]benzonitrile oxalate a) 4-Chloro-2-[[4-[[(1,1-dimethylethyl)dimethylsilyl]oxy]-1-(2-pyridinyl)butoxy]5-fluoro benzonitrile Sodium hydride (0.033 g, 60% dispersion in oil) was added to a solution of the product from Example 31 step (b) (0.214 g) and 4-chloro-2,5-difluorobenzonitrile (0.13 g) in tetrahydrofuran (5 ml) and the resultant suspension was stirred for 2 h. The mixture was quenched with aqueous ammonium chloride and basified to pH 8. The mixture was extracted with ethyl acetate (three times) and the combined organic extracts were dried (sodium sulphate) and evaporated to give an oil. Purification by chromatography on silica eluting with petrol-ether gave the sub-title compound as a colourless oil (0.31 g).

MS APCI+ve $^m$/z 435 ([M+H]$^+$).

b) 4-Chloro-5-fluoro-2-[4-hydroxy-1-(2-pyridinyl)butoxy]benzonitrile

The sub-title compound was prepared according to the method of Example 31 step (d) using the product of step (a) above.

MS APCI+ve $^m$/z 321 ([M+H]$^+$).

c) 4-Chloro-5-fluoro-2-[4-(methylamino)-1-(2-pyridinyl)butoxy]benzonitrile oxalate Triphenylphosphine (0.274 g) and N-iodosuccinimide (0.235 g) were added to a solution of the alcohol from step (b) (0.288 g) in tetrahydrofuran (4 ml) and the resultant solution was stirred for 2 h. Half of this solution was treated with 40% aqueous methylamine (3 ml) and the resultant solution was stirred for 60 h. The solvent was removed in vacuo and residue dissolved in water and extracted with dichloromethane three times. The combined organic extracts were washed with water, dried (magnesium sulphate) and evaporated to give an oil. Purification by chromatography on silica eluting with dichloromethane—3M ammonia in methanol gave a pale yellow gum (0.105 g). To a solution of this amine in ethanol (3 ml) was added a solution of oxalic acid (0.031 g) in ethanol (0.3 ml). The crystals that formed on cooling were collected and dried to afford the title compound as a white solid (0.091 g). M.p. 169–170° C.

MS APCI+ve $^m/z$ 334 ([M+H]$^+$).

$^1$H NMR 400 MHz (d$_6$-DMSO) 8.60 (d, 1H), 8.03 (d, 1H), 7.86 (td, 1H), 7.48 (d, 1H), 7.40 (d, 2H), 7.38–7.33 (m, 2H), 5.70 (t, 1H), 2.96 (t, 2H), 2.55 (s, 3H), 2.15–1.99 (m, 2H), 1.77–1.60 (m, 2H)

EXAMPLE 33

4-Chloro-2-[4-(ethylamino)-1-(2-pyridinyl)butoxy]benzonitrile oxalate a) 4-Chloro-2-[4-iodo-1-(2-pyridinyl)butoxy]benzonitrile A solution of the alcohol from Example 31 step (b) (0.1.75 g), triphenylphosphine (0.172 g) and N-iodosuccinimide (0.145 g) in dichloromethane (7 ml) was stirred for 1.5 h. Water was added and the The mixture was extracted with dichloromethane (three times) and the combined organic extracts were dried (magnesium sulphate), evaporated and purified by chromatography on silica silica eluting with petrol-ether to give the sub-title compound (0.114 g).

MS APCI+ve $^m/z$ 413 ([M+H]$^+$)

b) 4-Chloro-2-[4-(ethylamino)-1-(2-pyridinyl)butoxy]benzonitrile oxalate

A solution of the product from step (a) (0.108 g) in tetrahydrofuran (2 ml) and 70% aqueous ethylamine (1 ml) was stirred for 18 h. The solvent was removed in vacuo and residue dissolved in water and extracted with dichloromethane three times. The combined organic extracts were dried (magnesium sulphate) and evaporated to give an oil. Purification by chromatography on silica eluting with dichloromethane—3M ammonia in methanol gave a pale yellow gum (0.075 g). The oxalate salt was prepared as in Example 31 step (e) to afford the title compound as a white solid (0.047 g).

MS APCI+ve $^m/z$ 330 ([M+H]$^+$).

$^1$H NMR 400 MHz, (d$_6$-DMSO) δ8.60 (dd, 1H), 7.86 (td, 1H), 7.77 (d, 1H), 7.48 (d, 1H), 7.37 (t, 1H), 7.18–7.12 (m, 2H), 5.65 (t, 1H), 2.84 (t, 4H), 2.78 (q, 4H), 2.15–1.98 (m, 2H), 1.75–1.57 (m, 2H).

EXAMPLE 34

2-[4-Amino-1-(3-pyridinyl)butoxy]-4-chloro-benzonitrile oxalate a) 1-(3-Pyridinyl)-1 4-butanediol The sub-title compound was prepared by the method of Example 26 step (a) using pyridine-3-carboxaldehyde.

MS APCI+ve $^m/z$ 168 ([M+H]$^+$).

b) α-[3-[[(1,1-Dimethylethyl)dimethylsilyl]oxy]propyl]-3-pyridinemethanol

The sub-title compound was prepared by the method of Example 26 step (b) using the product of step (a) above.

MS APCI+ve $^m/z$ 282 ([M+H]$^+$).

c) 4-Chloro-2-[[4-[[(1,1-dimethylethyl)dimethylsilyl]oxy]-1-(3-pyridinyl)butoxy]benzonitrile The sub-title compound was prepared according to the method of Example 1 step (b) using the product of step (b) above and 4-chloro-2-hydroxybenzonitrile.

MS APCI+ve $^m/z$ 417 ([M+H]$^+$).

d) 4-Chloro-2-[4-hydroxy-1-(3-pyridinyl)butoxy]benzonitrile

40% Aqueous hydrofluoric acid (0.2 ml) was added to a solution of the product from step (c) (0.646 g) in acetonitrile (5 ml) at 0° C. and stirred for 1 h. Further hydrofluoric acid (0.2 ml) was added and stirring continued at 0° C. for 10hand at 20° C. for 4 h. Aqueous potassium carbonate was added, the mixture was extracted with ethyl acetate (three times) and the combined organic extracts were dried (sodium sulphate) and evaporated to give an oil. Purification by chromatography on silica eluting with dichloromethane—2M ammonia gave the sub-title compound as a white solid (0.426 g).

MS APCI+ve $^m/z$ 303 ([M+H]$^+$).

e) 2-[4-Amino-1-(3-pyridinyl)butoxy]-4-chlorobenzonitrile oxalate

Triphenylphosphine (0.142 g) and N-iodosuccinimide (0.124 g) were added to a solution of the alcohol from step (d) (0.134 g) in tetrahydrofuran (4 ml) and the resultant solution was stirred for 1.5 h. A solution of sodium iodide (0.044 g) in dimethylsulphoxide (0.2 ml) was added and stirred for 1.25 h. Triphenylphosphine (0.174 g) and water (0.5 ml) were added and stirred for 2 days. The solvent was partly removed in vacuo, aqueous sodium hydrogen carbonate added and the mixture extracted with dichloromethane. The combined organic extracts were dried (sodium sulphate), evaporated and purified by chromatography on silica eluting with dichloromethane—7M ammonia in methanol to give an orange gum (0.087 g). The oxalate salt was prepared as in Example 31 step (e) to afford the title compound as a white solid (0.047 g).

MS APCI+ve $^m/z$ 302 ([M+H]$^+$).

$^1$H NMR 400 MHz, (d$_6$-DMSO) 8.68 (d, 1H), 8.54 (d, 1H), 7.83 (d, 1H), 7.78 (d, 1H), 7.45 (dd, 1H), 7.40 (d, 1H), 7.16 (dd, 1H), 5.86 (t, 1H), 2.84 (t, 2H), 2.16–1.92 (m, 2H), 1.73–1.52 (m, 2H).

EXAMPLE 35

4-Chloro-2-[4-(methylamino)-1-(3-pyridinyl)butoxy]-benzonitrile oxalate

Triphenylphosphine (0.142 g) and N-iodosuccinimide (0.124 g) were added to a solution of the alcohol from Example 34 step (d) (0.134 g) in tetrahydrofuran (4 ml) and the resultant solution was stirred for 1.5 h. Methylamine was bubbled through for 2 minutes and the solution was then stirred for 2 days. The solvent was partly removed in vacuo, water added and the mixture extracted with dichloromethane. The combined organic extracts were dried (sodium sulphate), evaporated and purified by chromatography on silica eluting with dichloromethane—3M ammonia in methanol to give an orange gum (0.08 g). The oxalate salt was prepared as in Example 31 step (e) to afford the title compound as a white solid (0.093 g).

MS APCI+ve $^m/z$ 316 ([M+H]$^+$).

$^1$H NMR 300 MHz, (d$_6$-DMSO) 8.68 (s, 1H), 8.54 (t, 1H), 7.87–7.76 (m, 2H), 7.45 (t, 1H), 7.38 (s, 1H), 7.17 (d, 1H), 5.90–5.82 (m, 1H), 2.97 (t, 2H), 2.52 (t, 3H), 2.16–1.90 (m, 2H), 1.81–1.57 (m, 2H).

EXAMPLE 36

4-Chloro-2-[4-(ethylamino)-1-(4-pyridinyl)butoxy]-benzonitrile oxalate a) 1-(4-Pyridinyl)-1,4-butanediol The sub-title compound was prepared by the method of Example 31 step (a) using pyridine-4-carboxaldehyde.

MS APCI+ve $^m/z$ 168 ([M+H]$^+$).

b) α-[3-[[(1,1-Dimethylethyl)dimethylsilyl]oxy]propyl]-4-pyridinemethanol

The sub-title compound was prepared by the method of Example 31 step (b) using the product of step (a) above.

MS APCI+ve $^m/z$ 282 ([M+H]$^+$).

c) 4-Chloro-2-[[4-[[(1,1-dimethylethyl)dimethylsilyl]oxy]-1-(4-pyridinyl)butoxy]benzonitrile The sub-title compound was prepared according to the method of Example 1 step (b) using the product of step (b) above and 4-chloro-2-hydroxybenzonitrile.

MS APCI+ve $^m/z$ 417 ([M+H]$^+$).

d) 4-Chloro-2-[4-hydroxy-1-(4-pyridinyl)butoxy]benzonitrile

The sub-title compound was prepared according to the method of Example 31 step (d) using the product of step (c) above.

MS APCI+ve $^m/z$ 303 ([M+H]$^+$).

e) 4-Chloro-2-[4-(ethylamino)-1-(4-pyridinyl)butoxy]benzonitrile oxalate

The title compound was prepared according to the method of Example 31 step (e) using the product of step (d) above and 70% aqueous ethylamine.

MS APCI+ve $^m/z$ 330 ([M+H]$^+$).

$^1$H NMR 400 MHz (d$_6$-DMSO) 8.61 (t, 2H), 7.82 (dd, 1H), 7.41 (d, 2H), 7.27 (s, 1H), 7.18 (d, 1H), 5.84 (t, 1H), 3.00–2.85 (m, 4H), 2.07–1.93 (m, 2H), 1.76–1.61 (m, 2H), 1.15 (t, 3H).

EXAMPLE 37

4-Chloro-2-[4-(methylamino)-1-(4-pyridinyl)butoxy]benzonitrile oxalate

The title compound was prepared according to the method of Example 31 step (e) using the product of Example 36 step (d) and 40% aqueous methylamine. M.p. 169–172° C.

MS APCI+ve $^m/z$ 316 ([M+H]$^+$).

$^1$H NMR 300 MHz (d$_6$-DMSO) 8.60 (dd, 2H), 7.81 (d, 1H), 7.41 (d, 2H), 7.27 (d, 1H), 7.18 (dd, 1H), 5.83 (t, 1H), 2.94 (t, 2H), 2.50 (s, 3H), 2.11–1.89 (m, 2H), 1.77–1.59 (m, 2H).

EXAMPLE 38

4-Chloro-2-[4-[(2-hydroxyethyl)amino]-1-(4-pyridinyl)butoxy]benzonitrile oxalate Triphenylphosphine (0.137 g) and N-iodosuccinimide (0.118 g) were added to a solution of the alcohol from step (d) (0.144 g) in tetrahydrofuran (4 ml) and the resultant solution was stirred for 2 h. Ethanolamine (0.150 g) was added and the resultant solution was stirred for 24 h. The solvent was removed in vacuo and the residue was dissolved in water and extracted with dichloromethane three times. The combined organic extracts were washed with water, dried (magnesium sulphate) and evaporated to give an oil. Purification by chromatography on silica eluting with dichloromethane—3M ammonia in methanol gave a pale yellow gum (0.105 g). To a solution of this amine in 2-propanol (3 ml) was added a solution of oxalic acid (0.031 g) in methanol (0.3 ml). The crystals that formed on cooling were collected and dried to afford the title compound as a white solid (0.098 g).

MS APCI+ve $^m/z$ 346 ([M+H]$^+$).

$^1$H NMR 400 MHz (d$_6$-DMSO) 8.61 (d, 2H), 7.82 (d, 1H), 7.41 (d, 2H), 7.28 (s, 1H), 7.18 (d, 1H), 5.83 (t, 1H), 3.63 (t, 2H), 3.04–2.92 (m, 4H), 2.07–1.92 (m, 2H), 1.80–1.65 (m, 2H).

EXAMPLE 39

2-[4-Amino-1-(2-methoxy-3-pyridinyl)butoxy]-4-chlorobenzonitrile oxalate a) [4-(2-Methoxy-3-pyridinyl)-4-oxobutyl]carbamic acid 1,1-dimethylethyl ester 2-Methoxypyridine (1.9 ml) and then diisopropylamine (0.1 ml) were added to a solution of methyl lithium (10 ml of a 1.6M solution in ether) in tetrahydrofuran (20 ml) at −78° C. and the solution was stirred at 0° C. for 18hand then re-cooled to −78° C. A solution of 1,1-dimethylethyl [3-(methoxymethylamino)-3-oxopropyl]-carbamate (1.6 g) in tetrahydrofuran (5 ml) was added slowly and the resultant solution was allowed to warm to −30° C. over 3.5 h, quenched with aqueous ammonium chloride and extracted with ether (three times). The combined organic extracts were dried (sodium sulphate), evaporated and purified by chromatography on silica eluting with petrol-ether gave the sub-title compound as a colourless oil (0.572 g).

$^1$H NMR 300 MHz (CDCl$_3$) 8.30 (dd, 1H), 8.08 (dd, 1H), 6.98 (dd, 1H), 4.68–4.59 (m, 1H), 4.02 (d, 3H), 3.20 (q, 2H), 3.06 (t, 2H), 1.89 (quintet, 2H), 1.43 (s, 9H).

b) [4-Hydroxy-4-(2-methoxy-3-pyridinyl)butyl]carbamic acid 1,1-dimethylethyl ester Borane (0.7 ml, 1M in tetrahydrofuran) was added to a solution of (3aR)-tetrahydro-1-methyl-3,3-diphenyl-3H-pyrrolo[1,2-c][1,3,2]oxazaborole (0.05 ml, 1M in toluene) in tetrahydrofuran (2 ml) at 0° C. A solution of the product from step (a) above (0.304 g) in tetrahydrofuran (3 ml) was added over 20 minutes and then stirred at 0° C. for 4hand at 20° C. for 14 h. Methanol was added and the solution was evaporated and the residue azeotroped with methanol. Purification by chromatography on silica eluting with petrol-ether gave the sub-title compound as a colourless oil (0.255 g).

$^1$H NMR 300 MHz (CDCl$_3$) 8.07 (dd, 1H), 7.62 (d, 1H), 6.89 (t, 1H), 4.83 (q, 1H), 4.67–4.58 (m, 1H), 3.99 (m, 3H), 3.26–3.09 (m, 2H), 2.79–2.70 (m, 1H), 1.83–1.50 (m, 4H), 1.44 (d, 9H).

c) [4-(5-Chloro-2-cyanophenoxy)-4-(2-methoxy-3-pyridinyl)butyl]carbamic acid 1,1-dimethylethyl ester The sub-title compound was prepared by the method of Example 1 step (b) using the product of step (b) above and 4-chloro-2-hydroxybenzonitrile.

$^1$H NMR 300 MHz (CDCl$_3$) 8.13 (dd, 1H), 8.06–7.98 (m, 1H), 7.64 (dd, 1H), 7.44 (t, 1H), 7.03–6.76 (m, 1H), 5.55 (dd, 1H), 4.64–4.55 (m, 1H), 4.06 (s, 3H), 3.99–3.92 (m, 2H), 3.63–3.56 (m, 1H), 3.23–3.11 (m, 2H), 2.09–1.51 (m, 2H), 1.43 (s, 9H).

d) 2-[4-Amino-1-(2-methoxy-3-pyridinyl)butoxy]-4-chlorobenzonitrile oxalate

A solution of the product from step (c) (0.136 g) in 4M hydrogen chloride in dioxan (2 ml) was stirred for 1 h. Aqueous potassium carbonate was added and the mixture was extracted with dichloromethane. The organic extracts were dried (sodium sulphate), evaporated and purified by chromatography on silica eluting with dichloromethane—3M ammonia in methanol to give a pale yellow gum (0.073 g). The oxalate salt was prepared as in Example 31 step (e) to give the title compound as a white solid (0.065 g).

MS APCI+ve $^m/z$ 332 ([M+H]$^+$).

$^1$H NMR 400 MHz (d$_6$-DMSO) 8.16 (dd, 1H), 7.79 (d, 1H), 7.71 (dd, 1H), 7.16 (dd, 1H), 7.12 (d, 1H), 7.05 (dd, 1H), 5.77 (t, 1H), 3.97 (s, 3H), 2.85 (t, 2H), 2.13–1.94 (m, 2H), 1.74–1.55 (m, 2H).

EXAMPLE 40

2-[4-Amino-1-(1,2-dihydro-2-oxo-3-pyridinyl)butoxy]-4-chlorobenzonitrile oxalate A solution of the product from Example 39 step (d) (0.190 g) in ethanol (0.5 ml) and 4M hydrogen chloride in dioxan (2.5 ml) was stirred for 6 days. Aqueous potassium carbonate was added and the mixture was extracted with ethyl acetate and dichloromethane. The combined organic extracts were dried (sodium sulphate), evaporated and purified by chromatography on silica eluting with dichloromethane—7M ammonia in methanol gave a pale yellow gum (0.028 g). The oxalate salt was prepared as in Example 31 step (e) to give the title compound as a white solid (0.015 g).

MS APCI+ve $^m$/z 318 ([M+H]$^+$).

$^1$H NMR 400 MHz (d$_6$-DMSO) 7.79 (d, 1H), 7.60 (dddd, 1H), 7.52–7.46 (m, 2H), 7.42 (dddd, 1H), 7.19–7.13 (m, 2H), 6.27 (dt, 2H), 5.61 (t, 1H), 4.41 (t, 1H), 3.27–3.21 (m, 2H), 2.06–1.87 (m, 4H).

EXAMPLE 41
2-[[(1R)-4-amino-1-(3-furanyl)butyl]oxy]-4-chloro-5-fluoro-benzonitrile fumarate a) [4-(3-Furanyl)-4-oxobutyl]carbamic acid 1,1-dimethylethyl ester A solution of 3-bromofuran (4.3 g) in dry tetrahydrofuran (25 ml) was cooled to −70° C. under an atmosphere of nitrogen. A solution of 1,1-dimethylethyl-[4-(methoxymethylamino)-4-oxobutyl]-carbamate (3.4 g) in dry tetrahydrofuran (50 ml) was added dropwise and the reaction mixture was kept at −70° C. for 3 h. The reaction was quenched with saturated aqueous ammonium chloride (100 ml) and extracted into ethyl acetate (3×75 ml). The organic extract was washed with water, brine, dried over magnesium sulphate and evaporated to give an oil. This was passed down a silica gel column eluted with hexane:ethyl acetate (4:1) to afford the product as a clear oil (2.1 g).

$^1$H NMR 400 MHz (CDCl$_3$) 8.06–8.01 (1H, m), 7.44 (1H, t), 6.76 (1H, dd), 4.63 (1H, s), 3.24–3.13 (2H, m), 2.80 (2H, t), 1.91 (2H, quintet), 1.43 (9H, s).

b) [(4R)-4-(3-Furanyl)-4-hydroxybutyl]carbamic acid 1,1-dimethylethyl ester

The product from step (a) (1.8 g) was reduced by the same procedure described in Example 30 step (b) to afford the product as a clear gum (1.5 g).

$^1$H NMR 300 MHz (CDCl$_3$) 7.39 (2H, d), 6.40 (1H, t), 4.79–4.63 (1H, m), 4.65–4.49 (1H, m), 3.30–3.01 (2H, m), 1.87–1.69 (2H, m), 1.67–1.50 (2H, m), 1.62 (1H, d), 1.45 (9H, s).

c) [(4R)-4-(5-Chloro-2-cyano-4-fluorophenoxy)-4-(3-furanyl)butyl]carbamic acid 1,1-dimethylethyl ester The product from step (b) (1.4 g) was subjected to the procedure described in Example 30 step (c) to afford the product as a clear gum (1.5 g).

$^1$H NMR 300 MHz (CDCl$_3$) 7.43–7.39 (2H, m), 7.30 (1H, d), 6.99 (1H, d), 6.41 (1H, m), 5.24(1H, t), 4.57(1H, s), 3.33–3.03(2H, m), 2.19–2.02(1H, m), 2.01–1.84(1H, m), 1.77–1.60 (2H, m), 1.41 (9H, s).

d) 2-[[(1R)-4-Amino-1-(3-furanyl)butyl]oxy]-4-chloro-5-fluoro-benzonitrile fumarate The product from step (c) (0.2 g) was stirred in a mixture of dichloromethane (10 ml) and trifluoroacetic acid for 10 minutes. The reaction mixture was diluted with dichloromethane (50 ml) and washed with saturated sodium bicarbonate solution (100 ml), water, brine, dried over magnesium sulphate and evaporated to a clear oil. This was passed down a silica gel column eluted with dichloromethane containing 10% of 7N ammonia in methanol. The product was converted into the fumarate salt to afford a white solid (0.035 g).

MS APCI+ve $^m$/z 309 ([M+H]$^+$).

$^1$H NMR 400 MHz (d$_6$-DMSO) 7.97 (1H, d), 7.78 (1H, s), 7.72–7.59 (2H, m), 6.51 (1H, s), 6.42 (2H, s), 5.66 (1H, m), 2.92–2.76 (1H, m), 2.15–1.99 (1H, m), 1.99–1.83 (1H, m), 1.71–1.48 (2H, m).

EXAMPLE 42
4-Chloro-5-fluoro-2-[[(1R)-1-(3-furanyl)-4-(methylamino)butyl]oxy]benzonitrile fumarate a) [(4R)-4-(5-Chloro-2-cyano-4-fluorophenoxy)-4-(3-furanyl)butyl]methylcarbamic acid 1,1-dimethylethyl ester The product of Example 41 step (c) (0.68 g) was dissolved in dry tetrahydrofuran (40 ml) and treated with sodium hydride (60% dispersion in oil, 0.3 g) and stirred under nitrogen for 0.5 h. Methyl iodide (3 ml) was added and the reaction mixture stirred at ambient temperature for 48 h. The mixture was then cooled in an ice-bath and carefully treated with saturated ammonium chloride (50 ml) and extracted into ethyl acetate. The organic extract was washed with water, brine, dried over magnesium sulphate and evaporated to give a yellow oil (0.7 g).

$^1$H NMR 400 MHz (CDCl$_3$) 7.46–7.36 (2H, m), 7.30 (1H, d), 7.09–6.91 (1H, m), 6.41 (1H, s), 5.41–5.11 (1H, m), 3.42–3.16 (2H, m), 2.83 (3H, s), 2.16–1.94 (1H, m), 1.95–1.78 (1H, m), 1.79–1.62 (2H, m), 1.44 (9H, s).

b) 4-Chloro-5-fluoro-2-[[(1R)-1-(3-furanyl)-4-(methylamino)butyl]oxy]benzonitrile fumarate The product of step (a) (0.6 g) was subjected to the procedure described in Example 41 step (d) to afford the product as a fumarate salt (0.17 g).

MS APCI+ve $^m$/z 323 ([M+H]$^+$).

$^1$H NMR 300 MHz (d$_6$-DMSO) 7.97 (1H, d), 7.77 (1H, s), 7.68–7.60 (2H, m), 6.51 (1H, d), 6.43 (2H, s), 5.65 (1H, t), 2.89 (2H, t), 2.51 (3H, s), 2.10–1.98 (1H, m), 1.97–1.86 (1H, m), 1.76–1.55 (2H, m).

EXAMPLE 43
2-[4-Amino-1-(2-thiazolyl)butoxy]-4-chlorobenzonitrile hydrochloride a) [4-(Methoxymethylamino)-4-oxobutyl]carbamic acid 1,1-dimethylethyl ester 4-(Dimethylamino)pyridine (6.11 g), N,O-dimethylhydroxylamine hydrochloride (4.88 g), N-methylmorpholine (5.06 g) and 1-(3-dimethylaminopropyl)-3-ethylcarbodiimide hydrochloride (9.58 g) were added in quick succession to a solution of 4-(tert-butoxycarbonylamino)butyric acid (10.16 g) in dichloromethane (200 ml). The reaction mixture was then stirred under ambient conditions for 18 h. The solution was then washed with 2M hydrochloric acid solution, 10% sodium bicarbonate solution and brine. The organic layer was separated, dried over magnesium sulfate, filtered and the filtrate evaporated to dryness to give the subtitle compound as a colourless oil (10.2 g, 83%).

$^1$H NMR 300 MHz (CDCl$_3$) 4.73 (1H, s), 3.71 (3H, s), 3.19 (5H, s), 2.48 (2H, t), 1.83 (2H, quintet), 1.44 (9H, s).

b) [4-Oxo-4-(2-thiazolyl)butyl]carbamic acid 1,1-dimethylethyl ester

A solution of 2-bromothiazole (3.6 g) in dry tetrahydrofuran (100 ml) was cooled to −78° C. under an atmosphere of nitrogen. A 2.5M solution of n-butyllithium in hexane (8.8 ml) was added dropwise over 15 minutes maintaining the temperature below −60° C. The product from step (a) (2.46 g) in tetrahydrofuran (20 ml) was then added over 15 minutes again keeping the temperature below −60° C. The reaction mixture was then maintained at −70° C. for 1 h, then allowed to warm to −10° C. over 1.5 h. The reaction mixture was then partitioned between 10% ammonium chloride solution and ethyl acetate and the resulting colloid was filtered through celite. The organic extracts were dried over magnesium sulfate, filtered and the filtrate evaporated. The resulting dark brown oil was purified by flash chromatography, eluting with hexane:ethyl acetate (2:1) to give the subtitle compound as a pale yellow oil (0.9 g, 15%).

$^1$H NMR 400 MHz (CDCl$_3$) 8.00 (1H, d), 7.68 (1H, d), 4.69 (1H, br s), 3.21 (4H, m), 1.98 (2H, m), 1.42 (9H, s).

c) [4-Hydroxy-4-(2-thiazolyl)butyl]carbamic acid 1,1-dimethylethyl ester

The subtitle compound was prepared according to the method of Example 19 step (a) using the product of step (b) above.

$^1$H NMR 400 MHz (CDCl$_3$) 7.73 (1H, d), 7.30 (1H, d), 5.05 (1H, m), 4.15 (1H, s), 3.54 (1H, s), 3.19 (2H, m), 2.02 (1H, m), 1.88 (1H, m), 1.66 (2H, m), 1.44 (9H, s).

d) [4-(5-Chloro-2-cyanophenoxy)-4-(2-thiazolyl)butyl] carbamic acid 1,1-dimethylethyl ester The subtitle compound was prepared according to the method of Example 19 step (b) using the product of step (c) above and 2-hydroxy-4-chlorobenzonitrile.

MS APCI+ve$^m$/z 408 ([M+H]$^+$).

e) 2-[4-Amino-1-(2-thiazolyl)butoxy]-4-chlorobenzonitrile hydrochloride

The product from step (d) (0.20 g) was dissolved in 4M hydrochloric acid in dioxan (5 ml) and stirred for 3h at room temperature. The solvent was evaporated and the residue triturated with dry diethyl ether to give the title compound as a pale yellow solid (0.055 g). M.p 170–172° C.

$^1$H NMR 300 MHz (d$_6$-DMSO) 7.83 (6H, m), 7.54 (1H, s), 7.23 (1H, dd), 6.20 (1H, t), 2.86 (2H, m), 1.26 (2H, m), 1.72 (2H, m).

EXAMPLE 44

δ-[2-Chloro-5-(trifluoromethyl)phenoxy]-2-thiazolebutanamine oxalate a) [4-(2-Chloro-5-(trifluoromethyl)phenoxy)-4-(2-thiazolyl) butyl]carbamic acid 1,1-dimethylethyl ester The subtitle compound was prepared according to the method of Example 19 step (b) using the product of Example 43 step (c) and 2-chloro-5-trifluoromethylphenol.

MS APCI+ve$^m$/z 451 ([M+H]$^+$).

b) 8-[2-Chloro-5-(trifluoromethyl)phenoxy]-2-thiazolebutanamine oxalate

The product from step (a) (0.18 g) was dissolved in 4M hydrochloric acid in dioxan (5 ml) and stirred for 3h at room temperature. The solvent was evaporated and the residue was dissolved in methanol and treated with one equivalent of oxalic acid. The mixture was stirred for 10 minutes and then the solvent was removed in vacuo. The residue was triturated with dry diethyl ether and the off-white solid obtained was collected by filtration and dried to give the title compound (0.11 g). M.p. 164–166° C.

$^1$H NMR 300 MHz (d$_6$-DMSO) 7.85 (1H, d), 7.78 (1H, d), 7.70 (1H, d), 7.57 (1H, d), 7.35 (1H, dd), 6.17 (1H, t), 2.88 (2H, t), 2.18 (2H, m), 1.72 (2H, m).

EXAMPLE 45

2-[4-Amino-1-(1-methyl-1H-1,2,4-triazole-5-yl)butoxy-4-chlorobenzonitrile oxalate a) [4-(1-Methyl-1H-1,2,4-triazole-5-yl)-4-oxobutyl] carbamic acid 1,1-dimethylethyl ester The subtitle compound was prepared according to the method of Example 43 step (b) using the product of Example 43 step (a) and 1-methyl-1H-1,2,4-triazole.

$^1$H NMR 400 MHz (CDCl$_3$) 7.91 (1H, s), 4.67 (1H, s), 4.21 (3H, s), 3.20 (4H, m), 1.93 (2H, m), 1.43 (9H, s).

b) [4-Hydroxy-4-(1-methyl-1H-1,2,4-triazole-5-yl)butyl] carbamic acid 1,1-dimethylethyl ester The subtitle compound was prepared according to the method of Example 19 step (a) using the product of step (a) above.

$^1$H NMR 400 MHz (CDCl$_3$) 7.78 (1H, s), 4.91 (1H, s), 4.72 (1H, s), 3.95 (3H, s), 3.50 (1H, s), 3.21 (2H, s), 1.95 (2H, m), 1.67 (2H, m), 1.43 (9H, s).

c) [4-(5-Chloro-2-cyanophenoxy)]-4-(1-methyl-1H-1,2,4-triazole-5-yl)butyl]carbamic acid 1,1-dimethylethyl ester The subtitle compound was prepared according to the method of Example 19 step (b) using the product of step (b) above and 2-hydroxy-4-chlorobenzonitrile.

MS APCI+ve$^m$/z 406 ([M+H]$^+$).

d) 2-[4-Amino-1-(1-methyl-1H-1,2,4-triazole-5-yl) butoxy4-chlorobenzonitrile oxalate The title compound was prepared according to the method of Example 44 step (b) using the product of step (c) above. M.p. 163–165° C.

$^1$H NMR 400 MHz (d$_6$-DMSO) 7.97 (1H, s), 7.83 (1H, d), 7.77 (2H, s), 7.40 (1H, s), 7.24 (1H, d), 6.11 (1H, t), 3.94 (3H, s), 2.88 (2H, m), 2.16 (2H, m), 1.73 (1H, m), 1.60 (1H, m).

EXAMPLE 46

δ-[2-Chloro-5-(trifluoromethyl)phenoxy]-1-methyl-1H-1,2,4-triazole-5-butanamine hydrochloride a) [4-[2-Chloro-5-(trifluoromethyl)phenoxy)-1-4-(1-methyl-1H-1,2,4-triazole-5-yl)butyl]carbamic acid 1,1-dimethylethyl ester The subtitle compound was prepared according to the method of Example 19 step (b) using the product of Example 45 step (b) and 2-chloro-5-trifluoromethylphenol.

MS APCI+ve$^m$/z 449 ([M+H]$^+$).

b) 6-[2-Chloro-5-(trifluoromethyl)phenoxy]-1-methyl-1H-1,2,4-triazole-5-butanamine hydrochloride The title compound was prepared according to the method of Example 43 step (e) using the product of step (a) above. M.p. 179–181° C.

$^1$H NMR 400 MHz (d$_6$-DMSO) 7.95 (4H, s), 7.71 (1H, d), 7.41 (1H, s), 7.36 (1H, d), 6.10 (1H, m) 3.91 (3H, s), 2.87 (2H, m), 2.17 (2H, m), 1.79 (1H, m), 1.65 (1H, m).

Screens

The pharmacological activity of compounds according to the invention was tested in the following screens.

Screen 1

The activity of compounds of formula (I), or a pharmaceutically acceptable salt, enantiomer or racemate thereof, may be screened for nitric oxide synthase inhibiting activity by a procedure based on that of Förstermann et al., Eur. J. Pharm., 1992, 225; 161–165. Nitric oxide synthase converts $^3$H-L-arginine into $^3$H-L-citrulline which can be separated by cation exchange chromatography and quantified by liquid scintillation counting.

Enzyme is prepared, after induction, from the cultured murine macrophage cell line J774A-1 (obtained from the laboratories of the Imperial Cancer Research Fund). J774A-1 cells are cultured in Dulbeccos Modified Eagles Medium (D[MEM) supplemented with 10% foetal bovine serum, 4 mM L-glutamine and antibiotics (100 units/ml penicillin G, 100 mg/ml streptomycin & 0.25 mg/ml amphotericin B). Cells are routinely grown in 225 cm$^3$ flasks containing 35 ml medium kept at 37° C. and in a humidified atmosphere containing 5% CO$_2$.

Nitric oxide synthase is produced by cells in response to interferon-g (IFNg) and lipopolysaccharide (LPS). The medium from confluent culture flasks is removed and replaced with 25 ml (per flask) of fresh medium containing 1 mg/ml LPS and 10 units/ml IFNg. After a period of 17–20 hours in culture, harvesting of cells is accomplished by scraping the cell sheet from the flask surface into the culture medium. Cells are collected by centrifugation (1000 g for 10 minutes) and lysate prepared by adding to the cell pellet a solution containing 50 mM Tris-HCl (pH 7.5 at 20° C.), 10% (v/v) glycerol, 0.1% (v/v) Triton-X-100, 0.1 mM dithiothreitol and a cocktail of protease inhibitors comprising leupeptin (2 mg/ml), soya bean trypsin inhibitor (10 mg/ml), aprotinin (5 mg/ml) and phenylmethylsulphonyl fluoride (50 mg/ml).

For the assay, 25 μl of substrate cocktail (50 mM Tris-HCl (pH 7.5 at 20° C.), 400 μM NADPH, 20 μM flavin adenine dinucleotide, 20 μM flavin mononucleotide, 4 μM tetrahydrobiopterin, 12 μM L-arginine and 0.025 mCi L-[³H] arginine) is added to wells of a 96 well filter plate (0.45 μM pore size) containing 25 μl of a solution of test compound in 50 mM Tris-HCl. The reaction is started by adding 50 μl of cell lysate (prepared as above) and after incubation for 1 hour at room temperature is terminated by addition of 50 μl of an aqueous solution of 3 mM nitroarginine and 21 mM. EDTA.

Labelled L-citrulline is separated from labelled L-arginine using Dowex AG-50W. 150 μl of a 25% aqueous slurry of Dowex 50 W (Na⁺ form) is added to the assay after which the whole is filtered into 96 well plates. 75 μl of filtrate is sampled and added to wells of 96 well plates containing solid scintillant. After allowing the samples to dry the L-citrulline is quantified by scintillation counting.

In a typical experiment basal activity is 300 dpm per 75 μl sample which is increased to 1900 dpm in the reagent controls. Compound activity is expressed as $IC_{50}$ (the concentration of drug substance which gives 50% enzyme inhibition in the assay) and aminoguanidine, which gives an $IC_{50}$ (50% inhibitory concentration) of 10 μM, is tested as a standard to verify the procedure. Compounds are tested at a range of concentrations and from the inhibitions obtained $IC_{50}$ values are calculated. Compounds that inhibit the enzyme by at least 25% at 100 μM are classed as being active and are subjected to at least one retest.

Screen 2

Compounds also show activity against the human form of induced nitric oxide synthase as can be demonstrated in the following assay.

Enzyme is prepared, after induction, from the cultured human colon adrenocarcinoma cell line DLD1 (obtained from the European Collection of Animal Cell Culture—cell line number 90102540). DLD1 cells are cultured in RPMI 1640 medium supplemented with 10% foetal bovine serum, 4 mM L-glutamine and antibiotics (100 units/ml penicillin G, 100 μg/ml streptomycin and 0.25 μg/ml amphotericin B). Cells are routinely grown in 225 cm³ flasks containing 35 ml medium kept at 37° C. and in a humidified atmosphere containing 5% $CO_2$.

Nitric oxide synthase is produced by cells in response to interferon-γ (IFN-γ) and interleukin-1β (IL-1β). The medium from confluent flasks is removed and replaced with 25 ml (per flask) of fresh medium containing 250 units/ml IL-γ and 1000 units/ml IFN-γ. After a period of 17–20 hours in culture, harvesting of cells is accomplished by scraping the cell monolayer from the flask surface into the culture medium. Cells are collected by centrifugation (1000 g for 10 minutes) and lysate prepared by adding to the cell pellet a solution containing 50 mM Tris-HCl (pH 7.5 at 20° C.), 10% (v/v) glycerol, 0.1% (v/v) Triton-X100, 0.1 mM dithiothreitol and a cocktail of protease inhibitors including leupeptin (2 μg/ml), soya bean trypsin inhibitor (10 μg/ml), aprotonin (5 μg/ml) and phenylmethylsulphonyl fluoride (50 μg/ml).

For the assay, 25 μl of substrate cocktail (50 mM Tris-HCl (pH 7.5), 400 μM NADPH, 20 μM flavin adenine dinucleotide, 20 μM flavin mononucleotide and 4 μM tetrahydrobiopterin) is added to the wells of a 96-well plate. Test compounds are preincubated with enzyme by adding together with 40 μl of cell lysate (prepared as above) and incubating for 1 hour at 37° C. at the end of which period 10 μl of 30 μM L-arginine and 0.025 μCi of L-[³H]-arginine in 50 mM Tris-HCl is added to start the enzymatic reaction. Incubation is continued for a further 1 hour at 37° C. The reaction is terminated by addition of 50 μl of an aqueous solution of 3 mM nitroarginine and 21 mM EDTA.

Labelled L-citrulline is separated from labelled L-arginine using Dowex AG-50W. 120 μl of a 25% aqueous slurry of Dowex 50W is added to 96 well filter plates (0.45 μm pore size). To this is added 120 μl of terminated assay mix. 75 μl of filtrate is sampled and added to the wells of 96 well plates containing solid scintillant. After allowing the samples to dry the L-citrulline is quantified by scintillation counting.

In a typical experiment basal activity is 300 dpm per 75 μl sample of reagent controls, which is increased to 3000 dpm in the presence of enzyme. Compound activity is expressed as $IC_{50}$ (the concentration of drug substance which gives 50% enzyme inhibition in the assay) and L-NMMA, which gives an $IC_{50}$ of about 0.4 μM is tested as a standard to verify the procedure. Compounds are tested at a range of concentrations and from the inhibitions obtained $IC_{50}$ values are calculated.

When tested, the compounds of Examples 1 to 46, with the exception of Example 18, gave $IC_{50}$ values of less than 40 μM in at least one of the above screens, indicating that they are predicted to show useful therapeutic activity.

What is claimed is:

1. A compound of formula (I)

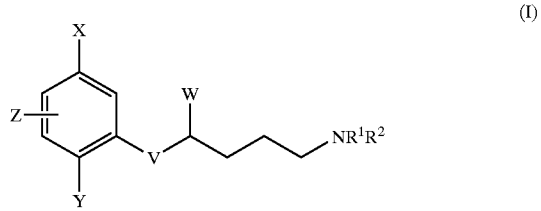

wherein:

X and Y independently represent C1 to 4 alkyl, C1 to 4 alkoxy, halogen, $CF_3$, $OCF_3$, CN, C≡CH, $S(O)_mCH_3$, $S(O)_pCF_3$, $NO_2$ or NHCHO;

m and p independently represent an integer 0, 1 or 2;

Z represents H or fluoro;

V represents O, $S(O)_n$ or $NR^3$;

W represents C1 to 4 alkyl, C2 to 4 alkenyl, C2 to 4 alkynyl, C3 to 6 cycloalkyl or a 4 to 8 membered saturated heterocyclic ring incorporating one heteroatom selected from O, S and N; any of said groups being optionally anther substituted by C1 to 4 alkyl, C1 to 4alkoxy, C1 to 4 alkylthio, C3 to 6 cycloalkyl, halogen or phenyl; said phenyl group being optionally further substituted by one or more substituents selected independently from halogen, C1 to 4 alkyl, C1 to 4 alkoxy, $CF_3$, $OCF_3$, CN or $NO_2$;

or W represents phenyl or a five or six membered aromatic heterocyclic ring containing 1 to 3 heteroatoms independently selected from O, S and N; said phenyl or aromatic heterocyclic ring being optionally substituted by one or more substituents selected independently from halogen, C1 to 4 alkyl, C1 to 4 alkoxy, OH, CN, $NO_2$ or $NR^4R^5$; said alkyl or alkoxy group being optionally further substituted by one or more fluorine atoms;

$R^1$ and $R^2$ independently represent H, C1 to 4 alkyl or C3 to 6 cycloalkyl; said alkyl group being optionally substituted by C1 to 4 alkoxy, halogen, hydroxy, $NR^6R^7$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, $CF_3$, $OCF_3$, CN or $NO_2$;

or the group $NR^1R^2$ together represents a 4 to 8 membered saturated azacyclic ring optionally incorporating one further heteroatom selected from O, S or NR$^8$; said ring being optionally substituted by C1 to 4 alkyl, C1 to 4 alkoxy or OH; said alkyl group being optionally substituted by C1 to 4 alkoxy, OH or NR$^9$R$^{10}$;

or the group NR$^1$R$^2$ together represents part of a five membered aromatic azacyclic ring optionally incorporating one further N atom;

R$^3$ represents H or C1 to 4 alkyl;

R$^4$, R$^5$, R$^6$, R$^7$, R$^9$ and R$^{10}$ independently represent H or C1 to 4 alkyl;

R$^8$ represents H or C1 to 6 alkyl; said alkyl group being optionally substituted by C1 to 4 alkoxy, OH, NR$^{11}$R$^{12}$, phenyl or a five or mix membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, CF$_3$, OCF$_3$, CN or NO$_2$;

R$^{11}$ and R$^{12}$ independently represent H or C1 to 4 alkyl;

n represents an integer 0, 1 or 2;

or a pharmaceutically acceptable salt, enantiomer or racemate thereof.

2. A compound of formula (I), according to claim 1, wherein V represents O.

3. A compound of formula (I), according to claim 1, wherein X and Y independently represent Br, Cl, CH$_3$, CF$_3$ or CN.

4. A compound of formula (I), according to claim 1, wherein W represents an optionally substituted five or six membered aromatic heterocyclic ring containing 1 to 3 heteroatoms independently selected from O, S and N.

5. A compound of formula (I), according to claim 1, wherein the substituents R$^1$ and R$^2$ are independently H or CH$_3$.

6. A compound of formula (I), according to claim 1, which is:

4-chloro-2-[[(1R)-4-(methylamino)-1-phenylbutyl]oxy]benzonitrile;

R-γ-(2,5-dichlorophenoxy)-N-methyl-benzenebutanamine;

4-chloro-2-[[(1R)-1-phenyl-4-(1-pyrrolidinyl)butyl]oxy]-benzonitrile;

4-chloro-2-[[(1R)-4-morpholinyl)-1-phenylbutyl]oxy]-benzonitrile;

4-chloro-2-[[(1R)-4-[ethyl(2-hydroxyethyl)amino]-1-phenylbutyl]oxy]-benzonitrile;

4-chloro-2-[[(1R)-1-phenyl-4-[(3-pyridinylmethyl)amino]butyl]oxy]-benzonitrile;

4-chloro-2-[[(1R)-4-(1H-imidazol-1-yl)-1-phenylbutyl]oxy]-benzonitrile;

4-chloro-2-[[(1R)-4-[(2-hydroxyethyl)amino]-1-phenylbutyl]oxy]-benzonitrile;

4-chloro-2-[[(1R)-4-(cyclopropylamino)-1-phenylbutyl]oxy]-benzonitrile;

4-chloro-2-[[(1R)-4-[(3-hydroxypropyl)amino]-1-phenylbutyl]oxy]-benzonitrile;

4-chloro-2-[[(1R)-4-[[(1R)-2-hydroxy-1-methylethyl]amino]-1-phenylbutyl]oxy]-benzonitrile;

4-chloro-2-[[(1R)-4-[[(1S)-2-hydroxy-1-methylethyl]amino]-1-phenylbutyl]oxy]-benzonitrile;

4-chloro-2-[4-[[(2-fluoroethyl)amino]-1-phenylbutyl]oxy]-benzonitrile;

R-δ-(2,5-dichlorophenoxy)-4-fluoro-N-methyl-benzenebutanamine;

S-δ-(2,5-dichlorophenoxy)-4-fluoro-N-methyl-benzenebutanamine;

R-γ-(2,5-dichlorophenoxy)-N,4-dimethyl-benzenebutanamine;

S-γ-(2,5-dichlorophenoxy)-N,4-dimethyl-benzenebutanamine;

δ-(2,5-dichlorophenoxy)-N-methyl-2-thiophenebutanamine;

2-[(4-amino-1-phenylbutyl)amino]-4-chloro-benzonitrile;

2-[[1-(3-aminopropyl)-3-methylbutyl]amino]-4-(trifluoromethyl)benzonitrile;

2-[[4-(2,5-dichlorophenoxy)-4-phenylbutyl]methylamino]ethanol;

1-[4-(2,5-dichlorophenoxy)-4-phenylbutyl]-4-piperidinol;

1-[4-(2,5-dichlorophenoxy)-4-phenylbutyl]piperazine;

1-[4-(2,5-dichlorophenoxy)-4-(2-thienyl)butyl]-4-methyl-piperazine;

4-chloro-2-[4-(methylamino)-1-(3-thienyl)butoxy]-benzonitrile;

4-chloro-2-[1-(3-furanyl)-4-(methylamino)butoxy]benzonitrile;

2-[4-amino-1-(3-furanyl)butoxy]-4-chlorobenzonitrile;

4-chloro-2-[1-(2-furanyl)-4-(methylamino)butoxy]benzonitrile;

2-[[(1R)-4-amino-1-(1-methyl-1H-imadazol-2-yl)butyl]oxy]-4-chloro-5-fluorobenzonitrile;

4-chloro-2-[4-(methylamino)-1-(2-pyridinyl)butoxy]benzonitrile;

4-chloro-5-fluoro-2-[4-(methylamino)-1-(2-pyridinyl)butoxy]benzonitrile;

4-chloro-2-[4-(ethylamino)-1-(2-pyridinyl)butoxy]benzonitrile;

2-[4-amino-1-(3-pyridinyl)butoxy]-4-chloro-benzonitrile;

4-chloro-2-[4-(methylamino)-1-(3-pyridinyl)butoxy]-benzonitrile;

4-chloro-2-[4-(ethylamino)-1-(4-pyridinyl)butoxy]-benzonitrile;

4-chloro-2-[4-(methylamino)-1-(4-pyridinyl)butoxy]-benzonitrile;

4-chloro-2-[4-(2-hydroxyethyl)amino]-1-(4-pyridinyl)butoxy]-benzonitrile;

2-[4-amino-1-(2-methoxy-3-pyridinyl)butoxy]-4-chloro-benzonitrile;

2-[4-amino-1-(1,2-dihydro-2-oxo-3-pyridinyl)butoxy]-4-chlorobenzonitrile;

2-[[(1R)-4-amino-1-(3-furanyl)butyl]oxy]-4-chloro-5-fluoro-benzonitrile;

4-chloro-5-fluoro-2-[[(1R)-1-(3-furanyl)-4-(methylamino)butyl]oxy]benzonitrile;

2-[4-amino-1-(2-thiazolyl)butoxy]4-chlorobenzonitrile;

δ-[2-chloro-5-(trifluoromethyl)phenoxy]-2-thiazolebutanamine;

2-[4-amino-1-(1-methyl-1H-1,2,4-triazole-5-yl)butoxy-4-chlorobenzonitrile;

δ-[2-chloro-5-(trifluoromethyl)phenoxy]-1-methyl-1H-1,2,4-triazole-5-butanamine;

or a pharmaceutically acceptable salt, enantiomer or racemate thereof.

7. A pharmaceutical composition comprising a compound of formula (I) according to claim 1, or a pharmaceutically acceptable salt, enantiomer or racemate thereof, in admixture with a pharmaceutically acceptable adjuvant, diluent or carrier.

8. A method of treating, or reducing the risk of, human diseases or conditions in which inhibition of nitric oxide synthase activity is beneficial which comprises administering a therapeutically effective amount of a compound of formula (I), as defined in claim 1, or a pharmaceutically acceptable salt, enantiomer or racemate thereof, to a person suffering from, or at increased risk of, such diseases or conditions.

9. A method of treatment according to claim 8 which it is predominantly inducible nitric oxide synthase that is inhibited.

10. A method of treating, or reducing the risk of, inflammatory disease in a person suffering from, or at risk of, said disease, wherein the method comprises administering to the person a therapeutically effective amount of a compound of formula (I), as defined in claim 1, or a pharmaceutically acceptable salt, enantiomer or racemate thereof.

11. The method of treatment as claimed in claim 10 wherein the disease is inflammatory bowel disease.

12. The method of treatment as claimed in claim 10 wherein the disease is rheumatoid arthritis.

13. The method of treatment as claimed in claim 10 wherein the disease is osteoarthritis.

14. A method of treating, or reducing the risk of, pain in a person suffering from, or at risk of, said condition, wherein the method comprises administering to the person a therapeutically effective amount of a compound of formula (I), as defined in claim 1, or a pharmaceutically acceptable salt, enantiomer or racemate thereof.

15. A method of treating, or reducing the risk of, inflammatory disease in a person suffering from, or at risk of, said disease, wherein the method comprises administering to the parson a therapeutically effective amount of a combination of a compound of formula (I), as defined in claim 1, or a pharmaceutically acceptable salt, enantiomer or racemate thereof, with a COX-2 inhibitor.

16. A process for the preparation of a compound of formula (I), as defined in claim 1, or a pharmaceutically acceptable salt, enantiomer or racemate thereof, wherein the process comprises:

(a) reaction of a compound of formula (II)

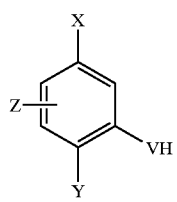

(II)

wherein X, Y, V and Z are as defined in claim 1, with a compound of formula (III)

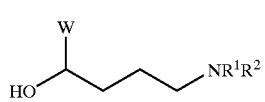

(III)

wherein W, $R^1$ and $R^2$ are as defined in claim 1; or (b) reaction of a compound of formula (IV)

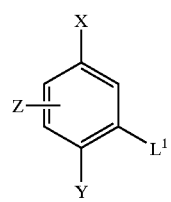

(IV)

wherein X, Y and Z are as defined in claim 1 and $L^1$ represents a leaving group, with a compound of formula (V)

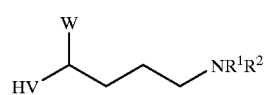

(V)

wherein $R^1$, $R^2$, V and W are as defined in claim 1; or (c) reaction of a compound of formula (VI)

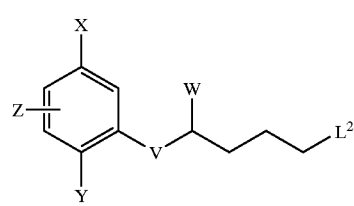

(VI)

wherein X, Y, V, W and Z are as defined in claim 1 and $L^2$ in a leaving group, with a compound of formula (VII)

$HNR^1R^2$  (VII)

wherein $R^1$ and $R^2$ are as defined in claim 1; or (d) reaction of a compound of formula (II)

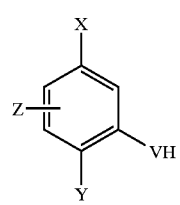

(II)

wherein X, Y, V and Z are as defined in claim 1, with a compound of formula (VIII)

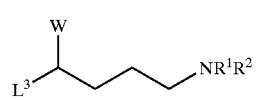

(VIII)

wherein $R^1$, $R^2$ and W are as defined in claim 1 and $L^3$ is a leaving group; or (e) reduction of a compound of formula (IX)

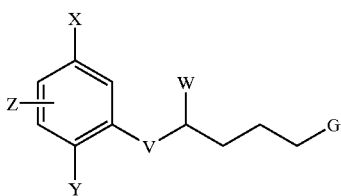

wherein X, Y, V, W and Z are as defined in claim 1 and G represents a group that upon reduction is converted into a group $NR^1R^2$;

and where necessary converting the resultant compound of formula (I), or another salt thereof, into a pharmaceutically acceptable salt thereof; or converting the resultant compound of formula (I) into a further compound of formula (I); and where desired converting the resultant compound of formula (I) into an optical isomer thereof.

17. A compound of formula (I), according to claim 1, wherein V represents O; and X and Y independently represent Br, Cl, $CH_3$, $CF_3$ or CN.

18. A compound of formula (I), according to claim 17, wherein W represents an optionally substituted five or six membered aromatic heterocyclic ring containing 1 to 3 heteroatoms independently selected from O, S and N.

19. A compound of formula (I), according to claim 18, wherein the substituents $R^1$ and $R^2$ are independently H or $CH_3$.

20. A pharmaceutical composition of claim 7 comprising the compound of formula (I) according to claim 18, or a pharmaceutically acceptable salt, enantiomer or racemate thereof, in admixture with a pharmaceutically acceptable adjuvant, diluent or carrier.

21. A pharmaceutical composition of claim 7 comprising a compound of formula (I) according to claim 6, or a pharmaceutically acceptable salt, enantiomer or racemate thereof, in admixture with a pharmaceutically acceptable adjuvant, diluent or carrier.

22. A method of treatment according to claim 8, which comprises administering a therapeutically effective amount of a compound of formula (I), at defined in claim 18, or a pharmaceutically acceptable salt, enantiomer or racemate thereof.

23. A method at treatment according to claim 8, which comprises administering a therapeutically effective amount of a compound of formula (I), as defined in claim 6, or a pharmaceutically acceptable salt, enantiomer or racemate thereof.

24. A method of treatment according to claim 10, which comprises administering a therapeutically effective amount of a compound of formula (I), as defined in claim 18, or a pharmaceutically acceptable salt, enantiomer or racemate thereof.

25. A method of treatment according to claim 10, which comprises administering a therapeutically effective amount of a compound of formula (I), as defined in claim 6, or a pharmaceutically acceptable salt, enantiomer or racemate thereof.

26. A method of treatment according to claim 14, which comprises administering a therapeutically effective amount of a compound of formula (I), as defined in claim 18, or a pharmaceutically acceptable salt, enantiomer or racemate thereof.

27. A method of treatment according to claim 14, which comprises administering a therapeutically effective amount of a compound of formula (I), as defined in claim 6, or a pharmaceutically acceptable salt, enantiomer or racemate thereof.

28. A method of treatment according to claim 15, which comprises administering a therapeutically effective amount of a compound of formula (I), as defined in claim 18, or a pharmaceutically acceptable salt, enantiomer or racemate thereof.

29. A method of treatment according to claim 15, which comprises administering a therapeutically effective amount of a compound of formula (I), as defined in claim 6, or a pharmaceutically acceptable salt, enantiomer or racemate thereof.

\* \* \* \* \*